United States Patent
Volpe et al.

(10) Patent No.: US 11,766,569 B2
(45) Date of Patent: Sep. 26, 2023

(54) PACING DEVICE WITH ACOUSTIC SENSOR

(71) Applicant: ZOLL MEDICAL CORPORATION, Chelmsford, MA (US)

(72) Inventors: Shane S. Volpe, Saltsburg, PA (US); Gregory R. Frank, Mt. Lebanon, PA (US); Thomas E. Kaib, North Huntingdon, PA (US); Steven J. Szymkiewicz, Bethel Park, PA (US); Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 186 days.

(21) Appl. No.: 17/498,946

(22) Filed: Oct. 12, 2021

(65) Prior Publication Data

US 2022/0054845 A1     Feb. 24, 2022

Related U.S. Application Data

(63) Continuation of application No. 16/229,483, filed on Dec. 21, 2018, now Pat. No. 11,179,570, which is a
(Continued)

(51) Int. Cl.
*A61N 1/37* (2006.01)
*A61N 1/365* (2006.01)
(Continued)

(52) U.S. Cl.
CPC .............. *A61N 1/371* (2013.01); *A61N 1/046* (2013.01); *A61N 1/0484* (2013.01);
(Continued)

(58) Field of Classification Search
CPC ...... A61N 1/371; A61N 1/046; A61N 1/0484; A61N 1/3625; A61N 1/36542; A61N 1/36578; A61N 1/3904; A61N 1/39044
See application file for complete search history.

(56) References Cited

U.S. PATENT DOCUMENTS

| | | | |
|---|---|---|---|
| 4,094,310 | A | 6/1978 | McEachern et al. |
| 4,632,122 | A | 12/1986 | Johansson et al. |

(Continued)

FOREIGN PATENT DOCUMENTS

| | | |
|---|---|---|
| DE | 2644236 C3 | 4/1981 |
| EP | 0295497 B1 | 9/1993 |

(Continued)

OTHER PUBLICATIONS

U.S. Appl. No. 16/229,483, filed Dec. 21, 2018, Pending.
(Continued)

*Primary Examiner* — Tammie K Marlen
(74) *Attorney, Agent, or Firm* — Finch & Maloney PLLC

(57) ABSTRACT

In at least one example, a medical device is provided. The medical device includes at least one therapy electrode, at least one acoustic sensor, and at least one processor coupled with the at least one therapy electrode and the at least one acoustic sensor. The at least one processor is configured to deliver at least one pacing pulse via the at least one therapy electrode and to analyze processed acoustic data to determine whether the at least one pacing pulse resulted in capture.

22 Claims, 14 Drawing Sheets

Related U.S. Application Data continuation of application No. 14/975,149, filed on Dec. 18, 2015, now Pat. No. 10,201,711.

(60) Provisional application No. 62/093,975, filed on Dec. 18, 2014.

(51) Int. Cl.
*A61N 1/04* (2006.01)
*A61N 1/362* (2006.01)
*A61N 1/39* (2006.01)

(52) U.S. Cl.
CPC ....... *A61N 1/3625* (2013.01); *A61N 1/36542* (2013.01); *A61N 1/36578* (2013.01); *A61N 1/3904* (2017.08); *A61N 1/39044* (2017.08)

(56) References Cited

U.S. PATENT DOCUMENTS

| | | | |
|---|---|---|---|
| 4,928,690 A | 5/1990 | Heilman et al. |
| 4,978,926 A | 12/1990 | Zerod et al. |
| 4,991,217 A | 2/1991 | Garrett et al. |
| 5,062,834 A | 11/1991 | Gross et al. |
| 5,078,134 A | 1/1992 | Heilman et al. |
| 5,348,008 A | 9/1994 | Bomn et al. |
| 5,365,932 A | 11/1994 | Greenhut |
| 5,381,798 A | 1/1995 | Burrows |
| 5,472,453 A | 12/1995 | Alt |
| 5,662,689 A | 9/1997 | Elsberry et al. |
| 5,718,242 A | 2/1998 | McClure et al. |
| 5,738,102 A | 4/1998 | Lemelson |
| 5,741,306 A | 4/1998 | Glegyak et al. |
| 5,758,443 A | 6/1998 | Pedrazzini |
| 5,792,190 A | 8/1998 | Olson et al. |
| 5,827,196 A | 10/1998 | Yeo et al. |
| 5,887,978 A | 3/1999 | Lunghofer et al. |
| 5,929,601 A | 7/1999 | Kaib et al. |
| 5,944,669 A | 8/1999 | Kaib et al. |
| 6,016,445 A | 1/2000 | Baura |
| 6,045,503 A | 4/2000 | Grabner et al. |
| 6,047,203 A | 4/2000 | Sackner et al. |
| 6,065,154 A | 5/2000 | Hulings et al. |
| 6,097,982 A | 8/2000 | Glegyak et al. |
| 6,097,987 A | 8/2000 | Milani |
| 6,148,233 A | 11/2000 | Owen et al. |
| 6,169,397 B1 | 1/2001 | Steinbach et al. |
| 6,253,099 B1 | 6/2001 | Oskin et al. |
| 6,280,461 B1 | 8/2001 | Glegyak et al. |
| 6,304,783 B1 | 10/2001 | Lyster et al. |
| 6,390,996 B1 | 5/2002 | Halperin et al. |
| 6,406,426 B1 | 6/2002 | Reuss et al. |
| 6,681,003 B2 | 1/2004 | Linder et al. |
| 6,690,969 B2 | 2/2004 | Bystrom et al. |
| 6,804,554 B2 | 10/2004 | Ujhelyi et al. |
| 6,827,695 B2 | 12/2004 | Palazzolo et al. |
| 6,878,121 B2 | 4/2005 | Krausman et al. |
| 6,908,437 B2 | 6/2005 | Bardy |
| 6,947,565 B2 | 9/2005 | Halleck et al. |
| 6,961,612 B2 | 11/2005 | Elghazzawi et al. |
| 6,990,373 B2 | 1/2006 | Jayne et al. |
| 7,149,579 B1 | 12/2006 | Koh et al. |
| 7,220,235 B2 | 5/2007 | Geheb et al. |
| 7,340,296 B2 | 3/2008 | Stahmann et al. |
| 7,453,354 B2 | 11/2008 | Reiter et al. |
| 7,488,293 B2 | 2/2009 | Marcovecchio et al. |
| 7,712,373 B2 | 5/2010 | Nagle et al. |
| 7,831,303 B2 | 11/2010 | Rueter et al. |
| 7,974,689 B2 | 7/2011 | Volpe et al. |
| 7,991,460 B2 | 8/2011 | Fischell et al. |
| 8,121,683 B2 | 2/2012 | Bucher et al. |
| 8,140,154 B2 | 3/2012 | Donnelly et al. |
| 8,271,082 B2 | 9/2012 | Donnelly et al. |
| 8,412,323 B2 | 4/2013 | Bauer |
| 9,320,906 B2 | 4/2016 | Maskara et al. |
| 10,201,711 B2 | 2/2019 | Volpe et al. |
| 10,321,877 B2 | 6/2019 | Volpe et al. |
| 2003/0004547 A1 | 1/2003 | Owen et al. |
| 2003/0060723 A1 | 3/2003 | Joo et al. |
| 2003/0095648 A1 | 5/2003 | Kaib et al. |
| 2003/0109904 A1 | 6/2003 | Silver et al. |
| 2003/0149462 A1 | 8/2003 | White et al. |
| 2003/0158593 A1 | 8/2003 | Heilman et al. |
| 2003/0174049 A1 | 9/2003 | Beigel et al. |
| 2003/0195567 A1 | 10/2003 | Jayne et al. |
| 2003/0212311 A1 | 11/2003 | Nova et al. |
| 2004/0049233 A1 | 3/2004 | Edwards |
| 2004/0162510 A1 | 8/2004 | Jayne et al. |
| 2004/0249419 A1 | 12/2004 | Chapman et al. |
| 2005/0049515 A1 | 3/2005 | Misczynski et al. |
| 2005/0131465 A1 | 6/2005 | Freeman et al. |
| 2005/0246199 A1 | 11/2005 | Futch |
| 2005/0283198 A1 | 12/2005 | Haubrich et al. |
| 2006/0036292 A1 | 2/2006 | Smith et al. |
| 2006/0085049 A1 | 4/2006 | Cory et al. |
| 2006/0178706 A1 | 8/2006 | Lisogurski et al. |
| 2006/0211934 A1 | 9/2006 | Hassonjee et al. |
| 2006/0270952 A1 | 11/2006 | Freeman et al. |
| 2006/0293714 A1 | 12/2006 | Salo et al. |
| 2007/0118056 A1 | 5/2007 | Wang et al. |
| 2007/0143864 A1 | 6/2007 | Cabana et al. |
| 2007/0161913 A1 | 7/2007 | Farrell et al. |
| 2007/0169364 A1 | 7/2007 | Townsend et al. |
| 2007/0197878 A1 | 8/2007 | Shklarski |
| 2007/0239214 A1 | 10/2007 | Cinbis |
| 2007/0239220 A1 | 10/2007 | Greenhut et al. |
| 2007/0265671 A1 | 11/2007 | Roberts et al. |
| 2008/0004536 A1 | 1/2008 | Baxi et al. |
| 2008/0021532 A1 | 1/2008 | Kveen et al. |
| 2008/0033495 A1 | 2/2008 | Kumar |
| 2008/0045815 A1 | 2/2008 | Derchak et al. |
| 2008/0046015 A1 | 2/2008 | Freeman et al. |
| 2008/0058884 A1 | 3/2008 | Matos |
| 2008/0103402 A1 | 5/2008 | Stickney et al. |
| 2008/0167535 A1 | 7/2008 | Stivoric et al. |
| 2008/0177341 A1 | 7/2008 | Bowers |
| 2008/0249591 A1 | 10/2008 | Gaw et al. |
| 2008/0287749 A1 | 11/2008 | Reuter |
| 2008/0294019 A1 | 11/2008 | Tran |
| 2008/0306560 A1 | 12/2008 | Macho et al. |
| 2008/0312520 A1 | 12/2008 | Rowlandson et al. |
| 2008/0312522 A1 | 12/2008 | Rowlandson et al. |
| 2008/0312709 A1 | 12/2008 | Volpe et al. |
| 2009/0018428 A1 | 1/2009 | Dais et al. |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0093687 A1 | 4/2009 | Telfort et al. |
| 2009/0138059 A1 | 5/2009 | Ouwerkerk |
| 2009/0146822 A1 | 6/2009 | Soliman |
| 2009/0234410 A1 | 9/2009 | Libbus et al. |
| 2009/0264792 A1 | 10/2009 | Mazar |
| 2009/0275848 A1 | 11/2009 | Brockway et al. |
| 2009/0281394 A1 | 11/2009 | Russell et al. |
| 2009/0287120 A1 | 11/2009 | Ferren et al. |
| 2009/0292194 A1 | 11/2009 | Libbus et al. |
| 2009/0295326 A1 | 12/2009 | Daynes et al. |
| 2009/0307266 A1 | 12/2009 | Fleizach et al. |
| 2009/0318779 A1 | 12/2009 | Tran |
| 2010/0052892 A1 | 3/2010 | Allen et al. |
| 2010/0052897 A1 | 3/2010 | Allen et al. |

(56) References Cited

U.S. PATENT DOCUMENTS

| | | | |
|---|---|---|---|
| 2010/0056881 A1 | 3/2010 | Libbus et al. |
| 2010/0069735 A1 | 3/2010 | Berkner |
| 2010/0076513 A1 | 3/2010 | Warren et al. |
| 2010/0081962 A1 | 4/2010 | Hamaguchi et al. |
| 2010/0114243 A1 | 5/2010 | Nowak et al. |
| 2010/0234716 A1 | 9/2010 | Engel |
| 2010/0241181 A1 | 9/2010 | Savage et al. |
| 2010/0295674 A1 | 11/2010 | Hsieh et al. |
| 2010/0298899 A1 | 11/2010 | Donnelly et al. |
| 2011/0015533 A1 | 1/2011 | Cox et al. |
| 2011/0093840 A1 | 4/2011 | Pynengurg et al. |
| 2011/0098765 A1 | 4/2011 | Patel |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0053479 A1 | 3/2012 | Hopenfeld |
| 2012/0112903 A1 | 5/2012 | Kaib et al. |
| 2012/0146797 A1 | 6/2012 | Oskin et al. |
| 2012/0150008 A1 | 6/2012 | Kaib et al. |
| 2012/0158075 A1 | 6/2012 | Kaib et al. |
| 2013/0060149 A1 | 3/2013 | Song et al. |
| 2013/0325078 A1 | 12/2013 | Whiting et al. |
| 2014/0088658 A1* | 3/2014 | Cheng | A61N 1/046 607/142 |
| 2014/0243918 A1* | 8/2014 | Sullivan | A61N 1/3937 607/6 |
| 2014/0277243 A1 | 9/2014 | Maskara et al. |
| 2015/0005588 A1 | 1/2015 | Herken et al. |
| 2016/0175598 A1 | 6/2016 | Volpe et al. |
| 2016/0270738 A1 | 9/2016 | Volpe et al. |
| 2019/0184177 A1 | 6/2019 | Volpe et al. |
| 2019/0246992 A1 | 8/2019 | Volpe et al. |

FOREIGN PATENT DOCUMENTS

| | | |
|---|---|---|
| EP | 0335356 B1 | 3/1996 |
| EP | 1455640 B1 | 1/2008 |
| EP | 1720446 B1 | 7/2010 |
| JP | 5115450 A | 5/1993 |
| JP | 2002200059 A | 7/2002 |
| WO | 200002484 A1 | 1/2000 |
| WO | 2004054656 A1 | 7/2004 |
| WO | 2004067083 A2 | 8/2004 |
| WO | 2004078259 A1 | 9/2004 |
| WO | 2005082454 A1 | 9/2005 |
| WO | 2006050325 A2 | 5/2006 |
| WO | 2007019325 A2 | 2/2007 |
| WO | 2009034506 A1 | 3/2009 |
| WO | 2010025432 A1 | 3/2010 |
| WO | 2010077997 A2 | 7/2010 |
| WO | 2014210179 A1 | 12/2014 |

OTHER PUBLICATIONS

U.S. Appl. No. 14/975,149, filed Dec. 18, 2015, Patented.

PCT Search Report and Written Opinion for PCT Application No. PCT/US2015/066852, dated May 4, 2016, 16 pages.

http://web.archiveorg/web/20030427001846/http/www.lifecor.com/imagelib/imageproduct.asp; Published by LifeCor, Inc., 2002, on webpage owned by LifeCor, Inc.

"ATS Statement: Guidelines for the Six-Minute Walk Test",American Journal of Respiratory and Critical Care Medicine, 2002, pp. 111-117, vol. 166, American Thoracic Society, , available at http://ajrccm.atsjournals.org/cgi/content/full/166/1/111.

O'Keeffe et al., "Reproductivity and Responsiveness of Quality of Life Assessment and Six Minute Walk Test in Elderly Heart Failure Patients", Heart, 1998, 80: 377-382.

De Bock et al., "Captopril Treatment if Chronic Heart Failure in the Very Old", Journal of Gerontology: Medical Sciences, 1994, pp. M148-M152, vol. 49, No. 3.

International Preliminary Report on Patentability (IPRP) received in PCT Application No. PCT/US2015/066852, dated Jun. 29, 2017, 8 pages.

PCT Search Report and Written Opinion for PCT Application No. PCT/US2016/023068, dated Jun. 3, 2016, 14 pages.

International Preliminary Report on Patentability (IPRP) received in PCT Application No. PCT/US2016/023068, dated Sep. 28, 2017, 9 pages.

\* cited by examiner

PACING DEVICE WITH ACOUSTIC SENSOR

RELATED APPLICATIONS

This application claims the benefit under 35 U.S.C. § 120 as a continuation of U.S. application Ser. No. 16/229,483, titled "PACING DEVICE WITH ACOUSTIC SENSOR," filed on Dec. 21, 2018, now U.S. Pat. No. 11,179,570 which is a continuation of U.S. application Ser. No. 14/975,149, titled "PACING DEVICE WITH ACOUSTIC SENSOR," filed on Dec. 18, 2015, now U.S. Pat. No. 10,201,711 which claims priority under 35 U.S.C. § 119(e) to U.S. Provisional Application Ser. No. 62/093,975, titled "PACING DEVICE WITH ACOUSTIC SENSOR," filed Dec. 18, 2014, each of which are hereby incorporated herein by reference in their entireties for all purposes.

BACKGROUND

Technical Field

This disclosure relates to medical devices, and more particularly to wearable pacing devices externally pacing the heart of a subject wearing the device.

Discussion

Cardiac arrest and other cardiac health ailments are a major cause of death worldwide. Various resuscitation efforts aim to maintain the body's circulatory and respiratory systems during cardiac arrest in an attempt to save the life of the victim. The sooner these resuscitation efforts begin, the better the victim's chances of survival.

To protect against cardiac arrest and other cardiac health ailments, some at-risk patients may use a wearable defibrillator, such as the LifeVest® wearable cardioverter defibrillator available from ZOLL Medical Corporation of Chelmsford, Mass. To remain protected, the patient wears the device nearly continuously while going about their normal daily activities, while awake, and while asleep.

SUMMARY

Some aspects disclosed herein manifest an appreciation for the sporadic inability of medical devices relying on conventional ECG sensing electrodes to correctly determine the cardiac function of a subject. For example, a pacing device in accord with at least one example disclosed herein utilizes a combination of electrode and acoustic sensor data to detect cardiac anomalies and function with increased accuracy and precision relative to conventional ECG sensing electrode based systems. With this enhanced cardiac data, various medical devices disclosed herein are better able to discriminate between detected cardiac anomalies that substantially impair cardiac function and those that do not. Using the enhanced cardiac data, these medical devices may modify the manner in which treatment is provided to a subject. For example, the medical devices may treat those anomalies that substantially impair cardiac function and may defer treatment where cardiac function is not substantially impaired.

In at least one example, a medical device is provided. The medical device may be an external medical device. The medical device includes at least one therapy electrode, at least one acoustic sensor, and at least one processor coupled with the at least one therapy electrode and the at least one acoustic sensor. The at least one processor is configured to deliver at least one pacing pulse via the at least one therapy electrode and to analyze processed acoustic data to determine whether the at least one pacing pulse resulted in capture.

In the medical device, the processed acoustic data may be based on acoustic signals recorded during a blanking interval. The at least one processor may be further configured to deliver another pacing pulse having an energy level higher than the at least one pacing pulse in response to determining that the at least one pacing pulse did not result in capture. The at least one processor may be further configured to deliver another pacing pulse having an energy level lower than the at least one pacing pulse in response to determining that the at least one pacing pulse resulted in capture. The at least one therapy electrode may include at least one first therapy electrode disposed on a front of a body of a subject and at least one second therapy electrode disposed on the front of the body of the subject.

In one example, a method of pacing a patient using an external medical device including at least one therapy electrode is provided. The method includes acts of delivering, by the external medical device, at least one pacing pulse via the at least one therapy electrode and analyzing, by the external medical device, processed acoustic data to determine whether the at least one pacing pulse resulted in capture.

In the method, the act of analyzing the processed acoustic data may include an act of recording acoustic signals during a blanking interval. The method may further include an act of delivering another pacing pulse having an energy level higher than the at least one pacing pulse in response to determining that the at least one pacing pulse did not result in capture. The method may further include an act of delivering another pacing pulse having an energy level lower than the at least one pacing pulse in response to determining that the at least one pacing pulse did result in capture.

In one example, a non-transitory computer readable medium storing executable instructions for pacing a subject is provided. The executable instructions including instructions that instruct at least one processor to deliver at least one pacing pulse via at least one therapy electrode and analyze processed acoustic data to determine whether the at least one pacing pulse resulted in capture. The instructions may further instruct the at least one processor to record acoustic signals during a blanking interval.

In one example, a wearable medical device is provided. The wearable medical device includes therapy electrodes and at least one processor in communication with the therapy electrodes. The therapy electrodes include at least one front therapy electrode disposed on a front of a body of a subject and at least one back therapy electrode disposed on a back of the body of the subject. The at least one processor can during a defibrillation mode, cause the at least one front therapy electrode to be cathodic and the at least one back therapy electrode to be anodic for a first phase of a biphasic defibrillation pulse and during a pacing mode, for at least one of a plurality of therapeutic phases of a pacing signal, cause the at least one front therapy electrode to be cathodic and the at least one back therapy electrode to be anodic.

In one example, a wearable medical device is provided. The wearable medical device includes therapy electrodes and at least one processor in communication with the therapy electrodes. The therapy electrodes comprise at least one front therapy electrode disposed on a front of a body of a subject and at least one back therapy electrode disposed on a back of the body of the subject. The at least one processor can during a defibrillation mode, cause the therapy electrodes to deliver a biphasic defibrillation pulse to the body of the subject and during a pacing mode, for at least one of a plurality of therapeutic phases of a pacing signal, cause a change in a polarity of the therapy electrodes such that the at least one front therapy electrode is used as an cathodic electrode and the at least one back therapy electrode is used as a anodic electrode.

In at least one example, a medical device is provided. The medical device includes at least one therapy electrode; at least one acoustic sensor; and at least one processor coupled with the at least one therapy electrode and the at least one acoustic sensor and configured to deliver at least one pacing pulse via the at least one therapy electrode and to analyze processed acoustic data to determine whether the at least one pacing pulse resulted in capture.

In the medical device, the at least one acoustic sensor may be configured to record one or more acoustic signals during a blanking interval and the processed acoustic data may be based on the one or more acoustic signals. The at least one processor may be further configured to deliver a pacing pulse having an energy level higher than the at least one pacing pulse in response to determining that the at least one pacing pulse did not result in capture. The at least one processor may be further configured to deliver a pacing pulse having an energy level lower than the at least one pacing pulse in response to determining that the at least one pacing pulse resulted in capture. The at least one processor may be further configured to deliver one or more pacing pulses having an energy level higher than the pacing pulse in response to determining that the pacing pulse did not result in capture. In the medical device, the at least one therapy electrode may include at least one first therapy electrode disposed on a front of a body of a subject and at least one second therapy electrode disposed on the front of the body of the subject.

In the medical device, the at least one processor may be further configured to determine whether a subject's level of discomfort exceeds a threshold and to deliver a pacing pulse having one or more adjusted attributes in response to determining that the level of discomfort exceeds the threshold. The medical device may further comprise a user interface. In the medical device, the at least one processor may be further configured to determine whether the subject's level of discomfort exceeds the threshold by analyzing information received via the user interface. The information may be descriptive of at least one of movement of the subject and vocalizations of the subject.

In the medical device, the one or more adjusted attributes may include at least one of an adjusted energy level, an adjusted width, and an adjusted rate. The medical device may further include a therapy electrode assembly comprising the therapy electrode and one or more reservoirs housing high impedance conductive gel. In the medical device, the at least one processor is configured to initiate deployment of the high impedance conductive gel via the therapy electrode assembly in response to determining that the level of discomfort exceeds the threshold.

In the medical device, the at least one processor may be further configured to detect a cardiac anomaly and identify a routine to address the cardiac anomaly. The medical device may further include a sensing electrode. In the medical device, the at least one acoustic sensor may be configured to record one or more acoustic signals while the sensing electrode is inoperable and the processed acoustic data may be based on the one or more acoustic signals.

In the medical device, the at least one processor may be configured to determine whether the at least one pacing pulse resulted in capture by detecting a threshold level of power in at least one acoustic signal represented in the processed acoustic data. The at least one processor may be configured to analyze the processed acoustic data at least in part by calculating a power spectrum of the processed acoustic data.

In at least one example, a medical device is provided. The medical device includes at least one therapy electrode; at least one acoustic sensor configured to record one or more acoustic signals during a blanking interval; at least one acoustic signal processor configured to generate processed acoustic data from the one or more acoustic signals; and at least one processor coupled with the at least one therapy electrode and the at least one acoustic sensor and configured to deliver at least one pacing pulse via the at least one therapy electrode and to analyze the processed acoustic data to determine whether power of at least one acoustic signal represented in the processed acoustic data falls within a predefined range of values.

In at least one example, a medical device is provided. The medical device includes a garment configured to be worn about a torso of a patient; at least one therapy electrode coupled to the garment; at least one acoustic sensor configured to record one or more acoustic signals; at least one acoustic signal processor configured to generate processed acoustic data from the one or more acoustic signals; and at least one processor coupled with the at least one therapy electrode and the at least one acoustic sensor and configured to deliver at least one pacing pulse via the at least one therapy electrode and to determine whether at least one value obtained from the processed acoustic data of at least one acoustic signal either transgresses a predefined threshold value or falls within a predefined range of values.

In the medical device, the at least one value may specify power of the at least one acoustic signal.

In at least one example, a method of pacing a subject using an external medical device is provided. The external medical device includes at least one therapy electrode. The method includes acts of delivering, by the external medical device, at least one pacing pulse via the at least one therapy electrode; and analyzing, by the external medical device, processed acoustic data to determine whether the at least one pacing pulse resulted in capture.

In the method, the act of analyzing the processed acoustic data may include an act of recording acoustic signals during a blanking interval.

In at least one example, a wearable medical device is provided. The wearable medical device includes therapy electrodes, wherein the therapy electrodes comprise at least one front therapy electrode disposed on a front of a body of a subject and at least one back therapy electrode disposed on a back of the body of the subject; and at least one processor coupled to the therapy electrodes, wherein the at least one processor can during a defibrillation mode, cause the at least one front therapy electrode to be cathodic and the at least one back therapy electrode to be anodic for a first phase of a biphasic defibrillation pulse; and during a pacing mode, for at least one of a plurality of therapeutic phases of a pacing signal, cause the at least one front therapy electrode to be cathodic and the at least one back therapy electrode to be anodic.

The wearable medical device may further include a circuit coupled to the at least one processor, the circuit including a plurality of switches configured to control whether the at least one front therapy electrode is cathodic or anodic and whether the at least one back therapy electrode is cathodic or anodic.

In the wearable medical device, the circuit may be an H-bridge circuit. The wearable medical device may further include at least one switch driver circuit configured to control a state of the plurality of switches.

In at least one example, a wearable medical device is provided. The wearable medical device includes therapy electrodes, wherein the therapy electrodes comprise at least one front therapy electrode disposed on a front of a body of a subject and at least one back therapy electrode disposed on a back of the body of the subject; and at least one processor coupled to the therapy electrodes, wherein the at least one processor can during a defibrillation mode, cause the therapy electrodes to deliver a biphasic defibrillation pulse to the body of the subject; and during a pacing mode, for at least one of a plurality of therapeutic phases of a pacing signal, cause a change in a polarity of the therapy electrodes such that the at least one front therapy electrode is used as an cathodic electrode and the at least one back therapy electrode is used as a anodic electrode.

The wearable medical device may further include a circuit coupled to the at least one processor, the circuit including a plurality of switches configured to control the polarity. The circuit may be an H-bridge circuit. The wearable medical device may further include at least one switch driver circuit configured to control a state of the plurality of switches.

Still other aspects, examples, and advantages of these exemplary aspects and examples, are discussed in detail below. Moreover, it is to be understood that both the foregoing information and the following detailed description are merely illustrative examples of various aspects, and are intended to provide an overview or framework for understanding the nature and character of the claimed subject matter. Any example disclosed herein may be combined with any other example. References to "an example," "some examples," "an alternate example," "various examples," "one example," "at least one example," "this and other examples" or the like are not necessarily mutually exclusive and are intended to indicate that a particular feature, structure, or characteristic described in connection with the example may be included in at least one example. The appearances of such terms herein are not necessarily all referring to the same example.

Furthermore, in the event of inconsistent usages of terms between this document and documents incorporated herein by reference, the term usage in the incorporated references is supplementary to that of this document; for irreconcilable inconsistencies, the term usage in this document controls. In addition, the accompanying drawings are included to provide illustration and a further understanding of the various aspects and examples, and are incorporated in and constitute a part of this specification. The drawings, together with the remainder of the specification, serve to explain principles and operations of the described and claimed aspects and examples.

BRIEF DESCRIPTION OF DRAWINGS

The accompanying drawings are not intended to be drawn to scale. In the drawings, components that are identical or nearly identical may be represented by a like numeral. For purposes of clarity, not every component is labeled in every drawing. In the drawings.

DETAILED DESCRIPTION

Figure 1:
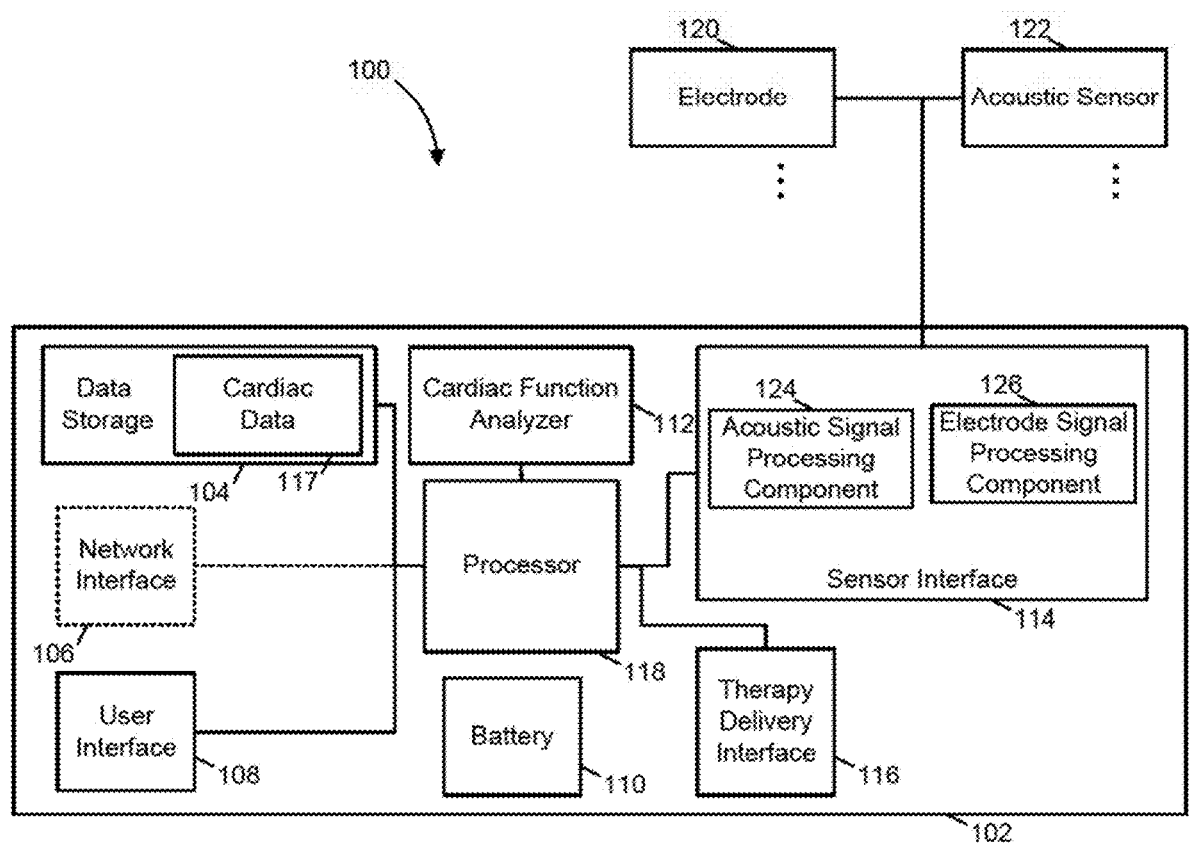
FIG. 1 is a functional schematic one example of a pacing device.

Medical devices in accord with various examples disclosed herein utilize enhanced cardiac data to implement a wide variety of functionality. For instance, according to some examples, a medical device includes a cardiac function analyzer configured to process enhanced cardiac data, which may include acoustic and electrode signals, to determine what type of treatment of a subject is warranted. In one example, a pacing device uses the enhanced cardiac data to determine whether a subject's cardiac rhythm has been successfully captured to prevent delivery of unduly painful energy levels.

Any of the medical devices disclosed herein may be external, non-invasive, bodily-attached, and/or ambulatory. External devices include devices that are disposed outside or substantially outside the patient's body and are in contrast to invasive, e.g., implantable, devices. For example, non-invasive devices include devices that do not penetrate the body of a subject. This is in contrast to invasive devices, such as implantable medical devices, in which at least a portion of the device is disposed subcutaneously. The term bodily-attached means that at least a portion of the device (other than its electrodes in the case of a defibrillator, cardioverter, or pacer) is removably attached to the body of a subject, such as by mechanical coupling (e.g., by a wrist strap, cervical collar, bicep ring), adhesion (e.g., by an adhesive gel intermediary), suction, magnetism, fabric or other flexible material (e.g., by straps or integration into a garment) or other body mounting features not limited by the aforementioned examples. These coupling elements hold the device in a substantially fixed position with respect to the body of the subject. The term ambulatory means that the device is capable of and designed for moving with the subject as the subject goes about their daily routine.

In some implementations, the medical device can be configured to monitor, in addition to cardiac signals, heart sounds, lung sounds, respiration, chest movements, and/or other patient body movement information. For example, such devices can be used as cardiac monitors in certain cardiac monitoring applications, such as holter monitoring, mobile cardiac telemetry (MCT) and/or continuous event monitoring (CEM) applications.

The examples of the methods and apparatuses discussed herein are not limited in application to the details of construction and the arrangement of components set forth in the following description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other examples.

Also, the phraseology and terminology used herein is for the purpose of description and should not be regarded as limiting. Any references to examples or elements or acts of the systems and methods herein referred to in the singular may also embrace examples including a plurality of these elements, and any references in plural to any example or element or act herein may also embrace examples including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Pacing Device

Various examples disclosed herein are configured to utilize enhanced cardiac data (e.g., acoustic data and electrode data) to detect and treat cardiac anomalies by delivering pacing pulses in accord with a variety of pacing routines. In some examples, a pacing device is implemented using a wearable defibrillator, such as the example wearable defibrillator described below with reference to FIG. 2. In some examples, a pacing device is implemented using an Automated External Defibrillator (AED), such as the example AED described below with reference to FIG. 4. In these examples, pacing devices are configured to perform a variety of different types of cardiac pacing to treat a wide variety of different cardiac arrhythmias, such as bradycardia, tachycardia, an irregular cardiac rhythm, pulseless electrical activity, or asystole (including asystole after a shock).

In some examples, the pacing device is configured to pace the heart of the subject at a fixed energy level (e.g., fixed current, fixed voltage, etc.) and pulse rate, to pace the heart of the subject on demand with a fixed energy level and an adjustable rate responsive to the detected intrinsic activity level of the subject's heart, or to pace the heart of the subject using capture management with an adjustable energy level and rate responsive to the detected intrinsic activity level of the subject's heart and the detected response of the subject's heart, including both on a beat-by-beat basis and as analyzed over other various time intervals. These various types of pacing may be applied to the subject externally by one or more of the therapy electrodes, such as the plurality of therapy electrodes 214 described below with reference to FIG. 2 or the one or more therapy electrodes 404 described below with reference to FIG. 4. Various types of pacing that can be performed by pacing device include asynchronous pacing at a fixed rate and energy, pacing on demand at a variable rate and fixed energy, and capture management pacing with an adjustable rate and adjustable energy level.

In some examples, the pacing device is configured to periodically assess the level of discomfort of a subject during pacing operation. In these examples, responsive to determining that the subject's discomfort level exceeds a threshold, the device may adjust the attributes of the pacing activity to lessen the discomfort experienced by the subject.

Figure 4:
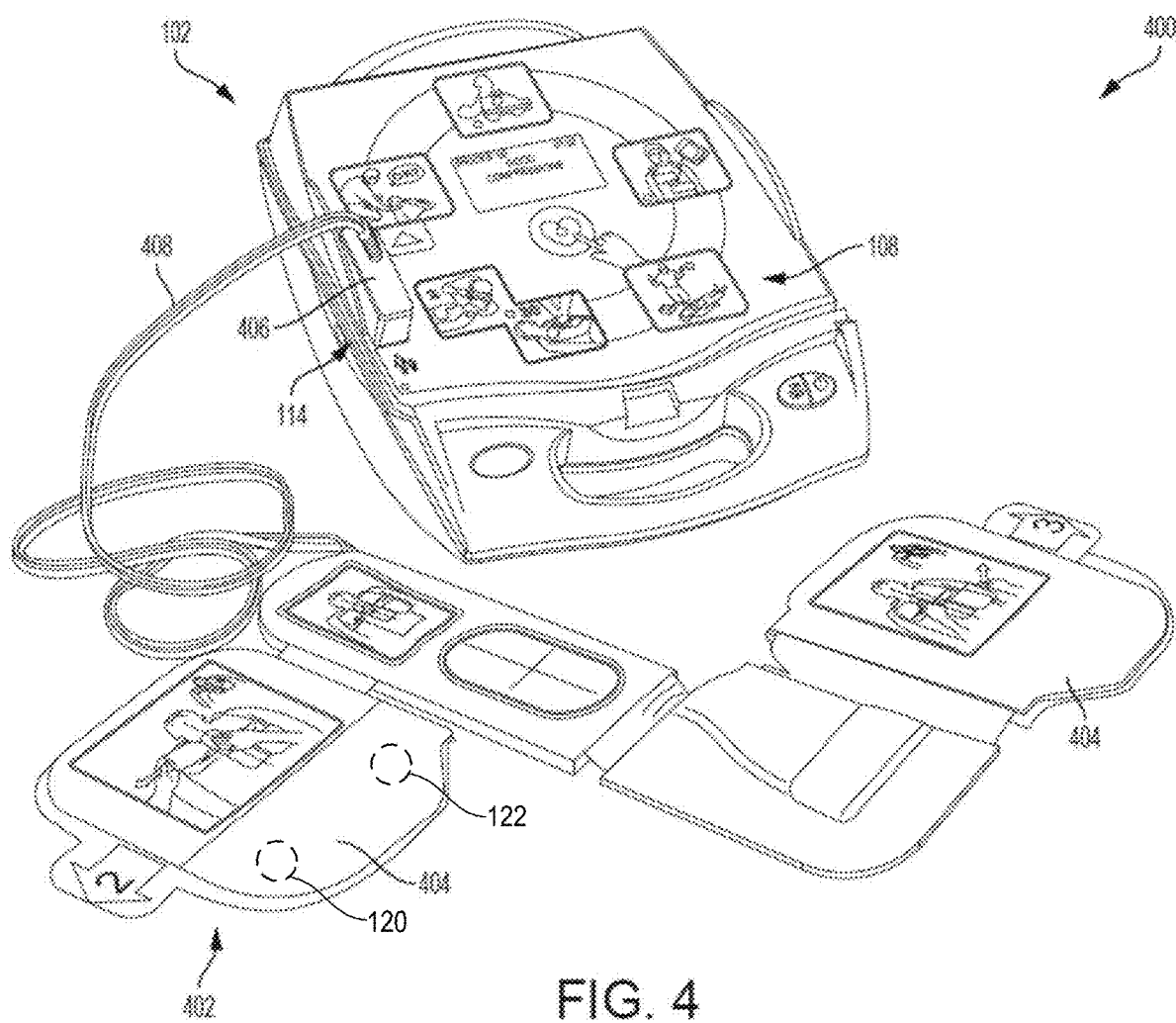
FIG. 4 is an illustration of one example of an external medical device.

In one example, the pacing device provides a user interface, such as the user interface 108 described below with reference to FIGS. 1 and 4, through which the pacing device receives information descriptive of the discomfort level experienced by a subject. Should this information indicate that the level of discomfort has transgressed a threshold level, the device adjusts characteristics of the pacing operation in an attempt to decrease the level of discomfort.

In one example, the pacing device assesses the level of discomfort of the subject by monitoring and recording the subject's movement before, during, and after administration of a pacing pulse. The device may monitor the subject's movement using a variety of instrumentation including, for example, one or more accelerators, acoustic sensors, etc. To assess the level of discomfort experienced by the subject during pacing pulses, the device may analyze the recorded history of the subject's movement and identify correlations between changes in the subject's movement and the pacing pulse. Strong correlations between pacing pulses and sudden subject movement, which may be representative of a flinch, and strong correlations between pacing pulses and a sudden stoppage of movement, may indicate that a subject is experiencing discomfort. The device may also analyze acoustic data to identify vocalizations indicative of pain (e.g., moans, shouts, and utterances) or movement and calculate correlations between pacing pulses and the vocalizations or movement. Correlations having a value that transgresses a threshold value may be deemed to indicate discomfort and may cause the device to adjust the characteristics of a pacing pulse.

In some examples, the device adjusts the characteristics of the pacing operation to lessen the discomfort level of the subject. The characteristics of the pacing operation that may be adjusted include, for example, the energy level of pacing pulses, the width of the pacing pulses, the rate of the pacing pulses, and the type of conductive gel dispensed for the pacing operation (e.g., gel having an impedance of 100 or more ohms). In some examples, the device monitors the cardiac activity of the subject during this adjustment process to ensure that the pacing operation continues to effectively manage cardiac function. In these examples, the device may revert the characteristics of the pacing operation to their previous settings, should the pacing operation become ineffective. Additional description of example pacing processes executed by the pacing device is provided further below with reference to FIGS. 5-8.

In some examples, a therapeutic device (e.g., a wearable defibrillator device that is pacing-enabled) can be configured to apply pacing pulses with one or more back electrodes of the plurality of electrodes acting as the positive electrode (or anodic electrode), and one or more front electrodes of the plurality of electrodes (e.g., electrodes located near the apex region of the heart) acting as the negative electrode (or cathodic electrode). Pacing thresholds are generally lower for cathodal stimulation of the ventricles. As such, to provide cathodal stimulation, e.g., by inducing polarization of the ventricles of the heart, the one or more front electrodes can be placed over the apex region of the heart. One or more back electrodes, acting as anodes, can be located on the back, for example, between the spine and the right scapula. In an implementation, a duration of a therapeutic pacing phase (e.g., a length of a therapeutic pacing pulse) can be within a range of approximately 2-120 ms.

In an example, hardware switches controlled by a medical device controller 102 (e.g., under software control) can be used to switch a polarity of the front and back electrodes during delivery of the pacing signals. For example, during a defibrillation mode, the controller 102 can cause the front electrode to be positive and the back electrode to be negative. In some examples, when the therapeutic device is in a pacing mode, the controller 102 can cause the front apex electrode to be designated as the cathode to effect cathodal stimulation, and the back electrode to be designated as the anode.

In some implementations, the pacing signal can include biphasic pulses. As such, the controller 102 can be configured such that during at least one of a plurality of phases of the pacing signal, the front apex electrode is designated as the cathode and the back electrode is designated as the anode.

Various circuit configurations may be employed in the pacing device to apply the pacing pulses to the patient in either direction (e.g., with the front electrodes acting as cathode and the back electrodes acting as anode, or vice versa). In one example, a pacing device can include an H-bridge circuit including four switches to control the direction of the pacing pulse as described in U.S. Pat. No. 8,909,335, titled "METHOD AND APPARATUS FOR APPLYING A RECTILINEAR BIPHASIC POWER WAVEFORM TO A LOAD," issued Dec. 9, 2014, which is hereby incorporated herein by reference in its entirety. In this example, a medical device controller 102 of the pacing device provides a phase profile indicative of the desired direction of the pacing pulse to one or more switch driver circuits that control the state of the four switches in the H-bridge to adjust the direction of current as indicated in the phase profile.

FIG. 1 illustrates a medical device 100 in accord with these examples. As shown in FIG. 1, the medical device 100 includes a medical device controller 102, one or more acoustic sensors 122, and one or more electrodes 120. The medical device controller 102 includes a processor 118, a sensor interface 114, a cardiac function analyzer 112, a therapy delivery interface 116, data storage 104, a communication network interface 106, a user interface 108, and a battery 110. The data storage 104 includes cardiac data 117. The sensor interface 114 includes an acoustic signal processing component 124 and an electrode signal processing component 126. The medical device 100 may be any of a variety of medical devices including defibrillators, eCPR systems, pacing devices, and other medical devices. Example medical devices are described further below with reference to FIGS. 2-4.

As shown in FIG. 1, the acoustic signal processing component 124 is coupled to and receives acoustic signals from the acoustic sensor 122. Similarly, the electrode signal processing component 126 is coupled to and receives electrode signals from the electrode 120. As illustrated in FIG. 1, the cardiac function analyzer 112 is coupled to and receives processed acoustic data from the acoustic signal processing component 124 and processed electrode data from the electrode signal processing component 126.

According to one example illustrated by FIG. 1, the cardiac function analyzer 112 is configured to detect both heartbeats and cardiac anomalies and determine whether the detected anomalies substantially impair cardiac function and thus require pacing. When executing according to this configuration, in some examples, the cardiac function analyzer 112 detects cardiac anomalies by scanning processed acoustic data and processed electrode data for patterns indicative of cardiac anomalies. Responsive to identifying a data pattern indicative of a cardiac anomaly, the cardiac function analyzer 112 identifies a routine to address the cardiac anomaly based on the identity of the anomaly and a confidence that the anomaly actually exists. Next, the cardiac function analyzer 112 initiates the identified routine. The data patterns scanned for by the cardiac function analyzer 112 are indicative of a wide variety of cardiac anomalies. Examples of these anomalies include cardiac arrhythmias (e.g., bradycardia, tachycardia, irregular cardiac rhythm, pulseless electrical activity, and asystole). The data patterns may also indicate problems with the medical device itself such as faulty or disconnected sensors.

In some examples, the cardiac function analyzer 112 is configured to leverage the differing originating modalities of the processed acoustic data and electrode data to advantageous effect. For instance, in one example, the cardiac function analyzer 112 analyzes processed acoustic data that covers periods of time for which processed electrode data is not available (e.g., due to an enforced blanking interval, temporary electrode saturation, or electrode fall off) and takes appropriate action based on the condition of a subject as indicated by the processed acoustic data. In some examples, the cardiac function analyzer 112 analyzes processed acoustic data representative of multiple signals. For instance, the cardiac function analyzer 112 may analyze data representative of a subject's respiration encoded from a first acoustic channel and data representative of a subject's heart sounds encoded from a second acoustic channel.

Examples in which the cardiac function analyzer 112 is configured to execute the actions described above are discussed further below with reference to FIGS. 2-4.

In some examples, the cardiac function analyzer 112 reads values of one or more configurable parameters that specify targeted operational characteristics of the cardiac function analyzer 112. These operational parameters may include upload filter criteria that specifies the data type and frequency with which the cardiac function analyzer 112 transmits enhanced cardiac data to a remote computer, such as the centralized server described further below with reference to FIG. 2 and the network interface 106.

In some examples illustrated by FIG. 1, the acoustic signal processing component 124 is configured to detect and record a variety of sounds related to cardiac function. To process analog and digital acoustic signals received from the acoustic sensor 122, the acoustic signal processing component 124 may include various circuitry, such as amplifiers, filters, transducers, analog to digital converters, analog signal processors, and digital signal processors. In at least one example, the acoustic signal processing component 124 processes signals received from a plurality of acoustic channels. Further according to some examples, the acoustic signal processing component 124 transmits processed acoustic data descriptive of the acoustic signals to the cardiac function analyzer 112 for subsequent analysis.

In healthy adults, there are at least two normal heart sounds, commonly referred to as S1 and S2. A third heart sound, commonly referred to as S3 (also called a protodiastolic gallop or ventricular gallop), may be indicative of a problem with a subject's heart when present. For example, in subjects over 40 years old, S3 has been associated with an abnormal diastolic filling pattern. The presence of S3 may signal cardiac problems like a failing left ventricle as in dilated congestive heart failure. A fourth heart sound, commonly referred to as S4 (also called a presystolic gallop or atrial gallop), is indicative of a problem with a subject's heart when present. For example, S4 is often associated with an increased left ventricular stiffness. Heart murmurs may also be present in some subjects and may indicate cardiac problems.

In some examples, the acoustic signal processing component 124 is configured to detect and record heart sound values including any one or all of S1, S2, S3, and S4. Other heart sound values which may be monitored and recorded by the acoustic signal processing component 124 may include any one or more of electromechanical activation time (EMAT), percentage of EMAT (% EMAT), systolic dysfunction index (SDI), and left ventricular systolic time (LVST). EMAT is generally measured from the onset of the Qwave on the ECG to the closure of the mitral valve within the S1 heart sound. Prolonged EMAT has been associated with reduced left ventricular ejection fraction (LV EF, being a measure of how much blood is being pumped out of the left ventricle of the heart with each contraction). % EMAT is EMAT divided by the dominant RR interval. % EMAT is related to the efficiency of the pump function of the heart. SDI is a multiplicative combination of ECG and heart sound values (EMA, S3, QRS duration and QR interval). SDI predicts left ventricular systolic dysfunction with high specificity. LVST is the systolic portion of the cardiac cycle and is defined as the time interval between the S1 and the S2 heart sounds. LVST has some heart rate dependence, and tends to be approximately 40% (range 30-50%) of the cardiac cycle but is affected by disease that produces poor contractility or a low ejection fraction.

In some examples, the acoustic signal processing component 124 reads values of one or more configurable parameters that specify targeted operational characteristics of the acoustic signal processing component 124 or the acoustic sensor 122. These operational parameters may specific the sampling rate, filter coefficients, recording duration and interval, and noise thresholds, and used to process acoustic data.

In one example illustrated by FIG. 1, the electrode signal processing component 126 is configured to detect and record cardiac activity of a subject. For example, when executing according to this configuration, the electrode signal processing component 126 may detect and record ECG signals. Further according to this example, the electrode signal processing component 126 transmits information descriptive of the ECG signals to the cardiac function analyzer 112 for subsequent analysis.

In one example illustrated by FIG. 1, the acoustic sensor 122 may comprise any device that may detect sounds from a subject's cardiac system and provide an output signal responsive to the detected heart sounds. In some examples the acoustic sensor 122 comprises a microphone. In some examples the acoustic sensor 122 comprises an accelerometer. The acoustic sensor 122 may comprise a microelectromechanical system (MEMS) accelerometer. In some examples the acoustic sensor 122 comprises a multi-channel accelerometer, for example, a three channel accelerometer. The acoustic sensor may comprise a three channel accelerometer configured to sense movement in each of three orthogonal axes. An example accelerometer which may be utilized in some examples is a LIS344ALH accelerometer, available from STMicroelectronics. The acoustic sensor 122 and associated electronics may be configured to monitor any one or more of a subject's heart sounds, a subject's position, and an activity level of a subject. The acoustic sensor 122 may provide signals indicative of the subject's heart sounds on a first channel, signals indicative of the subject's position on a second channel, and signals indicative of the subject's activity level on a third channel. In some examples, the different channels may be utilized to provide signals indicative of more than one physiological characteristic or other characteristics associated with the state of the subject. For example, in one example, the acoustic sensor 122 may provide signals indicative of the subject's heart sounds on a first channel, signals indicative of the subject's activity level on a second channel, and signals indicative of the subject's body position on any or all of the first, second, and a third channel. It should be appreciated that dependent on the underlying characteristic that is being monitored, multiple signals related to the characteristic being monitored may be received over a single channel or a number of different channels.

In one example illustrated by FIG. 1, the electrode 120 may include type of sensing electrode, such as one or more ECG sensing electrodes as described further below with reference to FIGS. 2 and 4.

In some examples in accord with FIG. 1, the battery 110 is a rechargeable 3 cell 2200 mAh lithium ion battery pack that provides electrical power to the other device components with a minimum 24 hour runtime between charges. It is appreciated that the battery capacity, runtime, and type (e.g., lithium ion, nickel-cadmium, or nickel-metal hydride) may be changed to best fit the specific application of the medical device controller 102.

According to the example illustrated in FIG. 1, the processor 118 is coupled to the sensor interface 114, the therapy delivery interface 116, the data storage 104, the network interface 106, and the user interface 108. The processor 118 performs a series of instructions that result in manipulated data which are stored in and retrieved from the data storage 104. According to a variety of examples, the processor 118 is a commercially available processor such as a processor manufactured by Texas Instruments, Intel, AMD, Sun, IBM, Motorola, Freescale, and ARM Holdings. However, the processor 118 may be any type of processor, multiprocessor or controller, whether commercially available or specially manufactured. For instance, according to one example, the processor 118 may include a power conserving processor arrangement as described in U.S. Pat. No. 8,904,214, titled "SYSTEM AND METHOD FOR CONSERVING POWER IN A MEDICAL DEVICE," issued Dec. 2, 2014, which is hereby incorporated herein by reference in its entirety. In one example, the processor 118 is an Intel® PXA270.

In addition, in several examples the processor 118 is configured to execute a conventional real-time operating system (RTOS), such as RTLinux. In these examples, the RTOS may provide platform services to application software, such as some examples of the cardiac function analyzer 112. These platform services may include inter-process and network communication, file system management and standard database manipulation. One or more of many operating systems may be used, and examples are not limited to any particular operating system or operating system characteristic. For instance, in some examples, the processor 118 may be configured to execute a non-real time operating system, such as BSD or GNU/Linux.

As illustrated in FIG. 1, the cardiac function analyzer 112, the acoustic signal processing component 124, and the electrode signal processing component 126 may be implemented using hardware or a combination of hardware and software. For instance, in one example, the cardiac function analyzer 112, the acoustic signal processing component 124, and the electrode signal processing component 126 are implemented as software components that are stored within the data storage 104 and executed by the processor 118. In this example, the instructions included in the cardiac function analyzer 112, the acoustic signal processing component 124, and the electrode signal processing component 126 program the processor 118 to analyze the cardiac function of a subject. In some examples, cardiac function analyzer 112, the acoustic signal processing component 124, and the electrode signal processing component 126 may be application-specific integrated circuits (ASICs) that are coupled to the processor 118 and tailored to analyze the cardiac function of a subject. Thus, examples of the cardiac function analyzer 112, the acoustic signal processing component 124, and the electrode signal processing component 126 are not limited to a particular hardware or software implementation.

In some examples, the components disclosed herein, such as the cardiac function analyzer 112, the acoustic signal processing component 124, and the electrode signal processing component 126 may read parameters that affect the functions performed by the components. These parameters may be physically stored in any form of suitable memory including volatile memory, such as RAM, or nonvolatile memory, such as a flash memory or magnetic hard drive. In addition, the parameters may be logically stored in a propriety data structure, such as a database or file defined by a user mode application, or in a commonly shared data structure, such as an application registry that is defined by an operating system. In addition, some examples provide for both system and user interfaces, as may be implemented using the user interface 108, that allow external entities to modify the parameters and thereby configure the behavior of the components.

The data storage 104 includes a computer readable and writeable nonvolatile data storage medium configured to store non-transitory instructions and data. In addition, the data storage 104 includes processor memory that stores data during operation of the processor 118. In some examples, the processor memory includes a relatively high performance, volatile, random access memory such as dynamic random access memory (DRAM), static memory (SRAM) or synchronous DRAM. However, the processor memory may include any device for storing data, such as a non-volatile memory, with sufficient throughput and storage capacity to support the functions described herein. According to several examples, the processor 118 causes data to be read from the nonvolatile data storage medium into the processor memory prior to processing the data. In these examples, the processor 118 copies the data from the processor memory to the non-volatile storage medium after processing is complete. A variety of components may manage data movement between the non-volatile storage medium and the processor memory and examples are not limited to particular data management components. Further, examples are not limited to a particular memory, memory system or data storage system.

The instructions stored on the data storage 104 may include executable programs or other code that can be executed by the processor 118. The instructions may be persistently stored as encoded signals, and the instructions may cause the processor 118 to perform the functions described herein. The data storage 104 also may include information that is recorded, on or in, the medium, and this information may be processed by the processor 118 during execution of instructions. The medium may, for example, be optical disk, magnetic disk or flash memory, among others, and may be permanently affixed to, or removable from, the medical device controller 102.

In some examples, the cardiac data 117 includes cardiac data detected, identified, and stored by the cardiac function analyzer 112. More particularly, according to the illustrated example, the cardiac data 117 includes information descriptive of cardiac function. For example, the cardiac data 117 may include ECG signal data, interpretations of the ECG signal data (e.g., heartbeats), analog heart sounds, acoustic signals, electrode signals, processed acoustic data, and processed electrode data.

As illustrated in FIG. 1, the cardiac function analyzer 112 and the cardiac data 117 are separate components. However, in some examples, the cardiac function analyzer 112 and the cardiac data 117 may be combined into a single component or re-organized so that a portion of the data included in the cardiac function analyzer 112, such as executable code that causes the processor 118 to analyze enhanced cardiac data, resides in the cardiac data 117, or vice versa. Such variations in these and the other components illustrated in FIG. 1 are intended to be within the scope of the examples disclosed herein.

The cardiac data 117 may be stored in any logical construction capable of storing information on a computer readable medium including, among other structures, flat files, indexed files, hierarchical databases, relational databases or object oriented databases. These data structures may be specifically configured to conserve storage space or increase data exchange performance. In addition, various examples organize the cardiac data 117 into particularized and, in some cases, unique structures to perform the functions disclosed herein. In these examples, the data structures are sized and arranged to store values for particular types of data, such as integers, floating point numbers, character strings, arrays, linked lists, and the like.

As shown in FIG. 1, the medical device controller 102 includes several system interface components 116, 106, and 114. Each of these system interface components is configured to exchange, i.e. send or receive, data with one or more specialized devices that may be located within the housing of the medical device controller 102 or elsewhere. The components used by the interfaces 116, 106, and 114 may include hardware components, software components, or a combination of both. Within each interface, these components physically and logically couple the medical device controller 102 to the specialized devices. This physical and logical coupling enables the medical device controller 102 to communicate with and, in some examples, power or control the operation of the specialized devices. These specialized devices may include physiological sensors, therapy delivery devices, and computer networking devices.

According to various examples, the hardware and software components of the interfaces 116, 106 and 114 implement a variety of coupling and communication techniques. In some examples, the interfaces 116, 106, and 114 use leads, cables or other wired connectors as conduits to exchange data between the medical device controller 102 and specialized devices. In some examples, the interfaces 116, 106, and 114 communicate with specialized devices using wireless technologies such as radio frequency or infrared technology. The software components included in the interfaces 116, 106, and 114 enable the processor 118 to communicate with specialized devices. These software components may include elements such as objects, executable code, and populated data structures. Together, these software components provide software interfaces through which the processor 118 can exchange information with specialized devices. Moreover, in at least some examples where one or more specialized devices communicate using analog signals, the interfaces 116, 106, and 114 further include components configured to convert analog information into digital information, and vice versa, to enable the processor 118 to communicate with specialized devices.

As discussed above, the system interface components 116, 106, and 114 shown in the example of FIG. 1 support different types of specialized devices. For instance, the components of the sensor interface 114 couple the processor 118 to one or more physiological sensors such as a body temperature sensors, respiration monitors, and ECG sensing electrodes, one or more environmental sensors such as atmospheric thermometers, airflow sensors, video sensors, acoustic sensors, accelerometers, GPS locators, and hygrometers. In these examples, the sensors may include sensors with a relatively low sampling rate, such as wireless sensors. Additionally, in at least one example, both the acoustic signal processing component 124 and the electrode signal processing component 126 described above with reference to FIG. 1 are integrated into the sensor interface 114.

The components of the therapy delivery interface 116 couple one or more therapy delivery devices, such as capacitors, defibrillator electrode assemblies, pacing electrode assemblies, or mechanical chest compression devices, to the processor 118. It is appreciated that the functionality of the therapy delivery interface 116 may be incorporated into the sensor interface 114 to form a single interface coupled to the processor 118. In addition, the components of the network interface 106 couple the processor 118 to a computer network via a networking device, such as a bridge, router or hub. According to a variety of examples, the network interface 106 supports a variety of standards and protocols, examples of which include USB (via, for example, a dongle to a computer), TCP/IP, Ethernet, Wireless Ethernet, Bluetooth, ZigBee, M-Bus, CAN-bus, IP, IPV6, UDP, DTN, HTTP, FTP, SNMP, CDMA, NMEA and GSM. It is appreciated that the network interface 106 of medical device controller 102 may enable communication between other medical device controllers within a certain range.

To ensure data transfer is secure, in some examples, the medical device controller 102 can transmit data via the network interface 106 using a variety of security measures including, for example, TLS, SSL, or VPN. In some examples, the network interface 106 includes both a physical interface configured for wireless communication and a physical interface configured for wired communication. According to various examples, the network interface 106 enables communication between the medical device controller 102 and a variety of personal electronic devices including computer enabled glasses and earpieces.

Thus, the various system interfaces incorporated in the medical device controller 102 allow the device to interoperate with a wide variety of devices in various contexts. For instance, some examples of the medical device controller 102 are configured to perform a process of sending critical events and data to a centralized server via the network interface 106. An illustration of a process in accord with these examples is disclosed in U.S. Pat. No. 6,681,003, titled "DATA COLLECTION AND SYSTEM MANAGEMENT FOR SUBJECT-WORN MEDICAL DEVICES," issued on Jan. 20, 2004, which is hereby incorporated herein by reference in its entirety.

As illustrated in FIG. 1, the network interface 106 is optional and may not be included in every example. For instance, an ambulatory defibrillator may include the medical device controller 102 to provide pacing functionality but may not include a network interface 106 where, for example, the ambulatory defibrillator is designed to rely on the user interface 108 to announce alarms.

The user interface 108 shown in FIG. 1 includes a combination of hardware and software components that allow the medical device controller 102 to communicate with an external entity, such as a subject or other user. These components may be configured to receive information from actions such as physical movement, verbal intonation or thought processes. In addition, the components of the user interface 108 can provide information to external entities. Examples of the components that may be employed within the user interface 108 include keyboards, mouse devices, trackballs, microphones, electrodes, touch screens, printing devices, display screens, and speakers. In some examples, the electrodes include an illuminating element, such as an LED. In some examples, the printing devices include printers capable of rendering visual or tactile (Braille) output.

Some examples may include a variety of features not shown in FIG. 1. For instance, although the acoustic sensor 122 and the electrode 120 are shown in FIG. 1 as one or more discrete sensors, some examples may integrate the electrode 120 and the acoustic sensor 122 into a single assembly. In some examples, the acoustic sensor 122 is integrated within a therapy electrode assembly. One such arrangement is described further in U.S. Patent Application Publication No. US 2015/0005588 A1, titled "THERAPEUTIC DEVICE INCLUDING ACOUSTIC SENSOR," published Jan. 1, 2015, which is hereby incorporated herein by reference in its entirety. In at least one example, the acoustic sensor 122 is integrated within a garment such as the garment described further below with reference to FIG. 2. For instance, the acoustic sensor 122 may be integrated within a belt, vest, or harness, such as the harness 110. Thus the examples disclosed herein are not limited to a particular number or arrangement of acoustic sensors or electrodes.

Example Ambulatory Medical Device

In some examples, the medical device 100 described above with reference to FIG. 1 is a wearable defibrillator that includes a garment (e.g., a vest or belt) that is worn by the subject. FIG. 2 illustrates a wearable defibrillator 200 in accord with these examples. In at least one example, the wearable defibrillator 200 may be a LifeVest® wearable cardioverter defibrillator available from ZOLL Medical Corporation of Chelmsford, Mass. The wearable defibrillator 200 monitors the subject's ECG with sensing electrodes, monitors the subject heart sounds with acoustic sensors, detects life-threatening arrhythmias, records events of interest, and delivers therapy in the form of one or more pacing pulses or a defibrillating shock through the therapy electrodes if treatment is necessary. As shown in FIG. 2, the wearable defibrillator 200 includes a harness 210 having a pair of shoulder straps and a belt that is worn about the torso of a subject. The wearable defibrillator 200 includes a plurality of ECG sensing electrodes 120 that are attached to the harness 210 at various positions about the subject's body and electrically coupled to the sensor interface 114 of the medical device controller 102 via a connection pod 220. The plurality of ECG sensing electrodes 120 are coupled to the medical device controller 102 to monitor the cardiac function of the subject and generally include a front/back pair of ECG sensing electrodes and a side/side pair of ECG sensing electrodes. The plurality of ECG sensing electrodes 120 may incorporate any electrode system, including conventional stick-on adhesive electrodes, dry-sensing capacitive ECG electrodes, radio transparent electrodes, segmented electrodes, or one or more long term wear electrodes that are configured to be continuously worn by a subject for extended periods (e.g., 3 or more days). One example of such a long term wear electrode is described in U.S. Patent Application Publication No. US 2013/0325096, titled "LONG TERM WEAR MULTIFUNCTION BIOMEDICAL ELECTRODE," published Dec. 5, 2013, which is hereby incorporated herein by reference in its entirety. Additional ECG sensing electrodes may be provided, and the plurality of ECG sensing electrodes 120 may be disposed at varying locations about the subject's body.

The wearable defibrillator 200 also includes one or more acoustic sensors 122 that are attached to a belt 250 of the harness 210 at various positions about the subject's body and electrically coupled to the sensor interface 114 of the medical device controller 102 via the connection pod 220. The one or more acoustic sensors 122 are coupled to the medical device controller 102 to monitor the cardiac function of the subject and generally include a front acoustic sensor and a back acoustic sensor.

Figure 2:
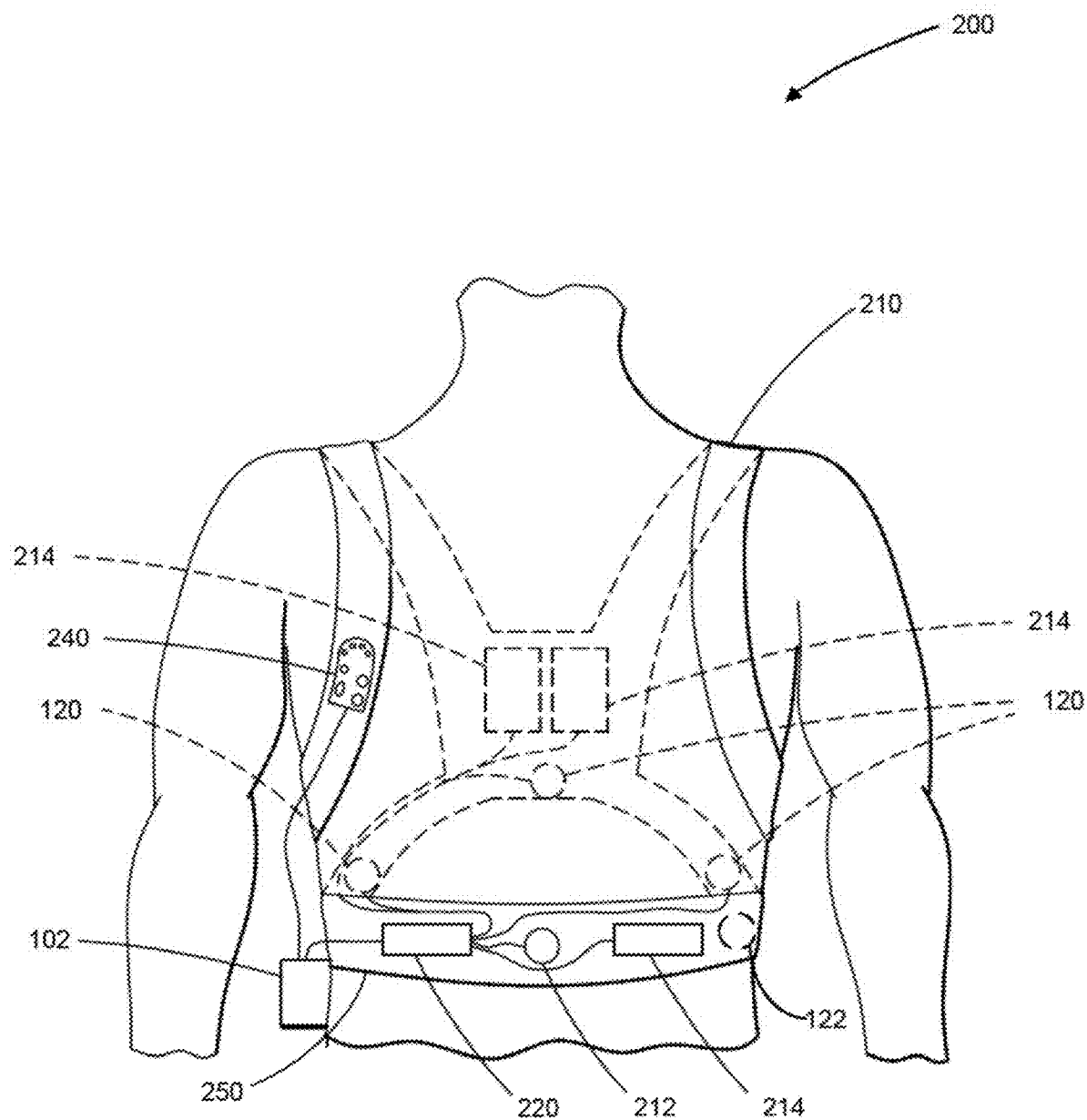
FIG. 2 is an illustration of one example of an ambulatory medical device.

Although not shown is FIG. 2, the wearable defibrillator 200 may include additional sensors, other than the plurality of ECG sensing electrodes 120, capable of monitoring the physiological condition or activity of the subject. For example, sensors capable of measuring blood pressure (via, for example, video blood pressure detection), heart rate, heart sounds, thoracic impedance, pulse oxygen level (via, for example, reflectance-based pulse oximetry to determine oxygen concentration), respiration rate, and the activity level of the subject may also be provided.

The wearable defibrillator 200 also includes a plurality of therapy electrodes 214 that are electrically coupled to the medical device controller 102 via the connection pod 220 and which are configured to deliver one or more therapeutic defibrillating shocks to the body of the subject, if it is determined that such treatment is warranted. Each therapy electrode of the plurality of therapy electrodes may be housed in a therapy electrode assembly that further includes conductive gel disposed within one or more reservoirs. Prior to delivering therapy, the therapy electrode assembly may dispense the conductive gel to improve conductivity between the therapy electrode and the body of the subject. The connection pod 220 electrically couples the plurality of ECG sensing electrodes 120 and the plurality of therapy electrodes 214 to the therapy delivery interface 116 of the medical device controller 102, and may include electronic circuitry configured for this purpose. The connection pod 220 may also include other electronic circuitry, such as a motion sensor or accelerometer through which subject activity may be monitored.

As shown in FIG. 2, the wearable defibrillator 200 also includes a user interface pod 240 that is electrically coupled to, or integrated in with, the user interface 108 of the medical device controller 102. The user interface pod 240 can be attached to the subject's clothing or to the harness 210, for example, via a clip (not shown) that is attached to a portion of the interface pod 240. In some examples, the user interface pod 240 may simply be held in a person's hand. In some examples, the user interface pod 240 may communicate wirelessly with the user interface 108 of the medical device controller 102, for example, using a Bluetooth®, Wireless USB, ZigBee, Wireless Ethernet, GSM, or other type of communication interface.

The user interface pod 240 includes a number of buttons by which the subject, or a bystander can communicate with the medical device controller 102, and a speaker by which the medical device controller 102 may communicate with the subject or the bystander. For example, where the medical device controller 102 determines that the subject is experiencing a cardiac arrhythmia, the medical device controller 102 may issue an audible alarm via a speaker on the medical device controller 102 or the user interface pod 240 alerting the subject and any bystanders to the subject's medical condition. The medical device controller 102 may also instruct the subject to press and hold one or more buttons on the user interface 108 of the medical device controller 102 or on the user interface pod 240 to indicate that the subject is conscious, thereby instructing the medical device controller 102 to withhold the delivery of one or more therapeutic defibrillating shocks. If the subject does not respond, the device may infer that the subject is unconscious, and proceed with the treatment sequence, culminating in the delivery of one or more defibrillating shocks to the body of the subject.

Figure 3B:
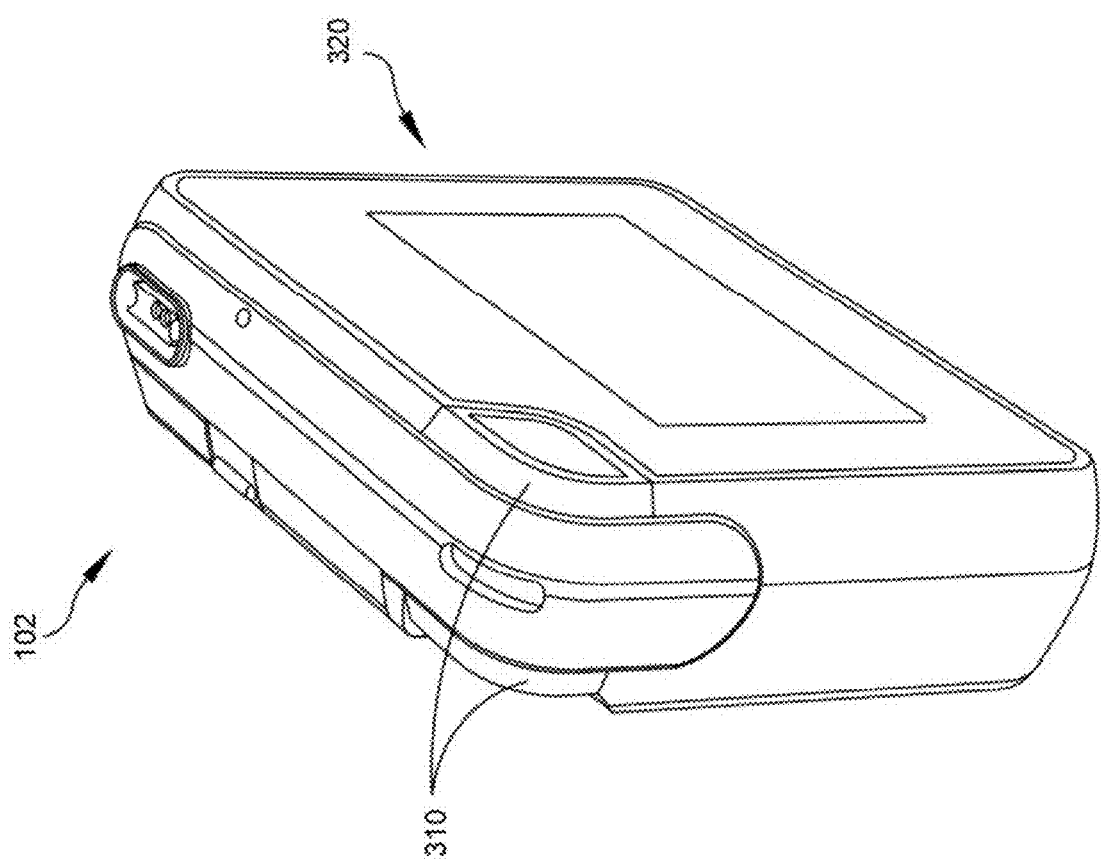
FIGS. 3A-B are illustrations of one example of a medical device controller for an ambulatory medical device.
Figure 3A:
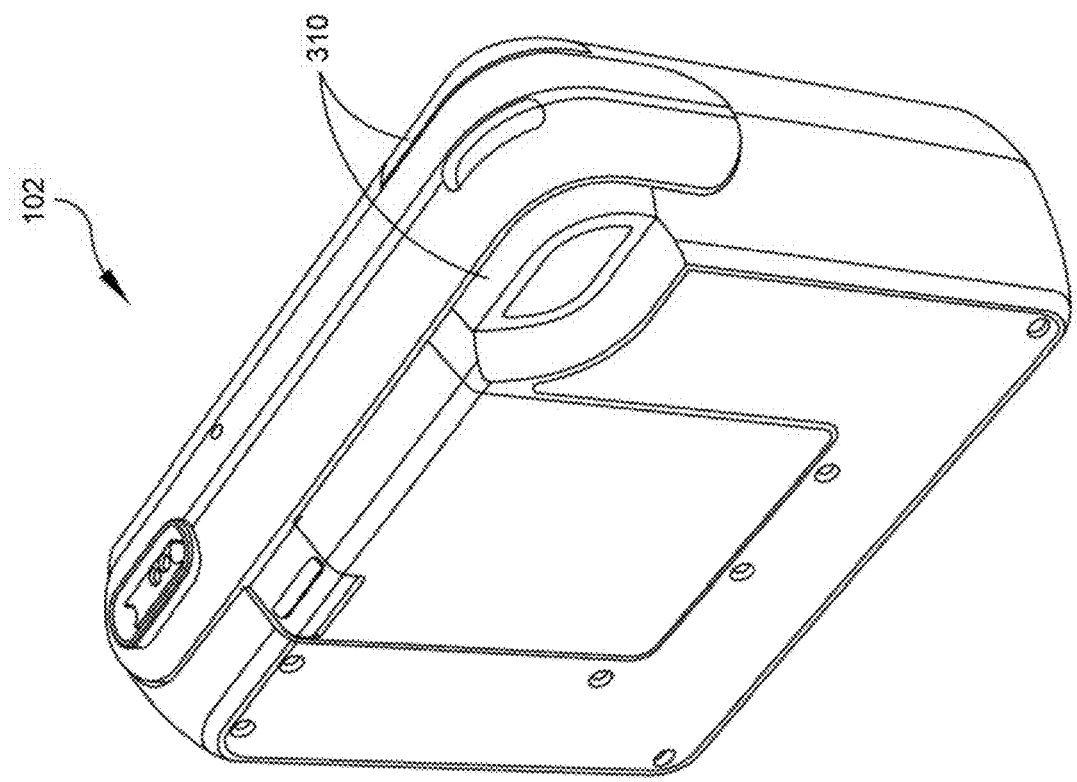

In one example, the functionality of the user interface pod 240 is integrated into the housing of the medical device controller 102. FIGS. 3A-B illustrate such an example of the medical device controller 102. The medical device controller 102 includes two response buttons 310 on opposing sides of the housing of the medical device controller 102. As shown in FIGS. 3A-B, the response buttons 310 are recessed to reduce the likelihood of accidental activation (e.g., a subject falling on the response button). The medical device controller 102 also includes, in this example, a display screen 320 and a speaker to enable the communication of audible and visual stimuli to the subject. It is appreciated that the response buttons 310 do not have to be placed on opposing sides of the housing as illustrated in FIGS. 3A-B. The response buttons, for example, may be located adjacent to each other in the housing the medical device controller 102. The adjacent placement of the response buttons may make it easier for individuals with smaller hands or less dexterity to engage the response buttons.

Example Automated Medical Device

In some examples, the medical device 100 described above with reference to FIG. 1 is an AED. AEDs are small portable defibrillators that are capable of monitoring cardiac rhythms, determining when a defibrillating shock is necessary, and administering the defibrillating shock either automatically, or under the control of a trained rescuer (e.g., an EMT or other medically training personnel). The AED, in addition, may be configured to provide counseling to an operator as to how to perform cardiac resuscitation (CPR). FIG. 4 illustrates an AED 400. The AED 400 may be, for example, an AED Plus® automated external defibrillator available from ZOLL Medical Corporation of Chelmsford, Mass. As shown, the AED 400 includes a medical device controller 102 and an electrode assembly 402.

The electrode assembly 402 includes one or more sensing electrodes 120 (e.g., ECG sensors), one or more acoustic sensors 122, one or more therapy electrodes 404 (e.g., defibrillation pads), a connector 406, wiring 408 electrically coupling the connector 406 to the one or more sensing electrodes 120, the one or more acoustic sensors, and the one or more therapy electrodes 404. As shown in FIG. 4, the connector is configured to couple the electrode assembly 402 to the medical device controller 102 and, more specifically, the one or more sensing electrodes 120 and the one or more acoustic sensors 122 to the sensor interface 114 and the one or more therapy electrodes to the therapy delivery interface 116.

The medical device controller 102 of the AED 400 is configured to detect the cardiac rhythm of the subject using ECG and heart sounds data and provide pacing and defibrillating shocks to the subject as appropriate. This process is similar to the process described with regard to medical device controller 102 of the ambulatory medical device 200. The user interface 108 of the AED 400 may include a variety of components configured to communicate with the operator including, but not limited to, a display screen, a speaker, and one or more buttons. In this example, the AED 400 includes a display screen to display notifications to an operator. The notifications may provide instructions to the operator regarding the proper administration of CPR to the subject. The notifications on the display may be accompanied by audible alerts from the speaker to further assist the operator in administering CPR to the subject.

Example Hospital Based Medical Device

Figure 14:
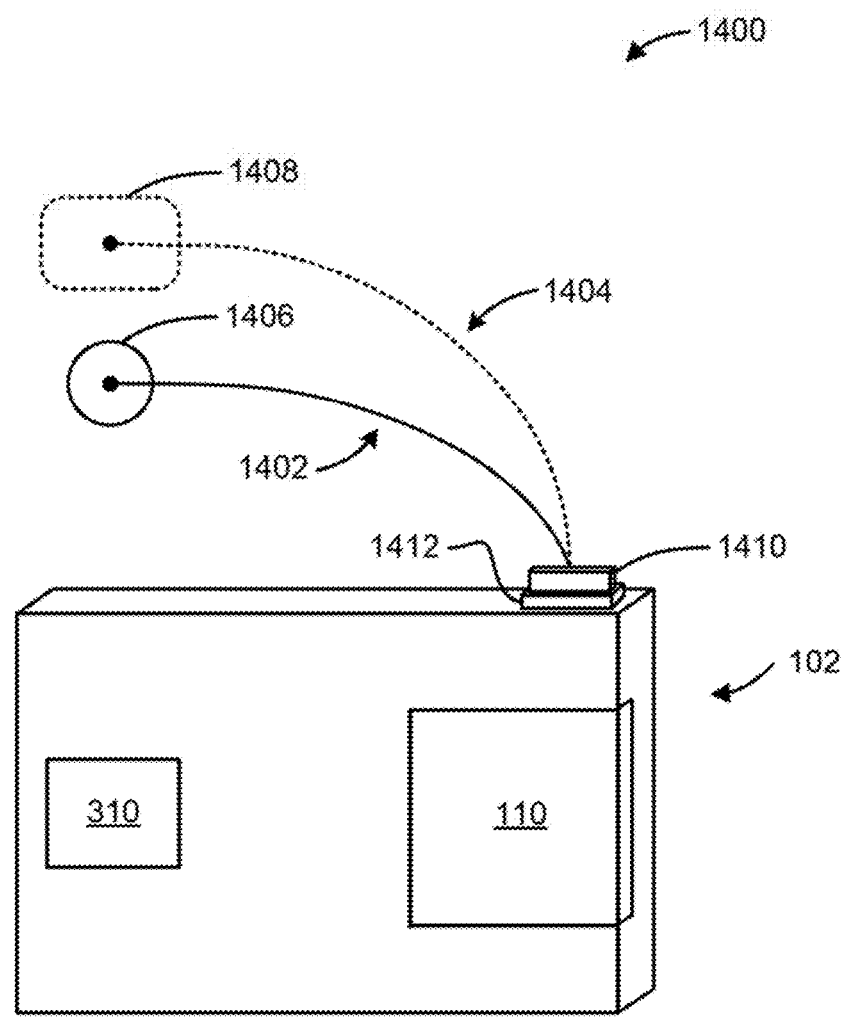
FIG. 14 is a schematic diagram of another example of a medical device.

In some examples, the medical device 100 described above with reference to FIG. 1 is a hospital based medical device. FIG. 14 illustrates an example hospital based medical device employing the medical device controller 102. As illustrated in FIG. 14, the hospital based medical device 1400 includes the medical device controller 102 and a sensing component 1402. The sensing component 1402 includes a connector 1410 constructed to removably couple to a port 1412 of the medical device controller 102. The sensing component 1402 may sense information indicative of cardiac activity of the patient including, for example, ECG activity, tissue fluid, lung fluid, lung sounds, heart sounds, and/or patient activity. In some examples, the sensing component 1402 includes one or more electrodes 1406. The electrodes 1406 may be stick-on adhesive electrodes constructed to attach to the patient. In some examples, the electrodes 1406 may be detachable from a wire lead coupling the electrode 1406 to the connector 1410. Constructing the sensing component 1402 to make the electrodes 1406 detachable may enable the patient and/or caregiver to periodically (e.g., every 24 hours) replace the electrodes 1406 without replacing the entire sensing component 1402. The electrodes 1406 may be long term wear electrodes that are configured to be continuously worn by a patient for extended periods (e.g., 3 or more days).

In some examples, the hospital based medical device 1400 may also include a treatment component 1404 to provide treatment to the patient. The treatment component 1404 may include, for example, a therapy pad 1408 configured to attach to the patient. The treatment component 1404 may be connected to the same connector 1410 as the sensing component 1402 and/or employ a separate connector that is capable of coupling to the connector 1410 in a modular fashion. It is appreciated that the treatment component 1404 may be integrated into the sensing component 1402 in a combined sensing treatment component.

Example Monitoring Medical Device

In some examples, an external medical device that can include the pacing and/or pacing capture detection techniques described herein may be a patient monitor for use in certain cardiac monitoring applications, such as holter monitoring, mobile cardiac telemetry (MCT) and/or continuous event monitoring (CEM) applications. Monitored cardiac information can include, without limitation, heart rate, ECG data, and heart sounds data from an acoustic sensor. In addition to cardiac monitoring, the cardiac monitor may be configured to monitor other patient parameters and physiological data, including glucose levels, blood oxygen levels, lung fluids, lung sounds, and blood pressure using various sensors, such as tissue fluid sensors, heart sounds sensors, lung sound sensors, and pulse oximetry sensors. In some implementations, the cardiac monitor is capable of and designed for being worn by a patient who is at risk of developing cardiac problems, but who does not yet meet criteria to be outfitted with a medical device that includes a treatment component (e.g., a defibrillator). Thus, the cardiac monitor may be prescribed so that continuous and/or event-based data can be sent from the cardiac monitor to a server (e.g., a remote server). A caregiver can access the data from the remote server and determine whether the patient is experiencing or has experienced a cardiac problem. In some implementations, after determining that the patient is experiencing a cardiac problem, the caregiver may instruct the patient to begin wearing a medical device with treatment capabilities. In some implementations, the patient can interact with a user interface of the cardiac monitor to identify a patient symptom. The user interface may include a touch-screen that provides a drop down menu or check list which, in turn, allows the patient to select a particular symptom from a list of alternatives. Options for patients can include one or more of: feeling a skipped beat, shortness of breath, light headedness, racing heart rate, fatigue, fainting, chest discomfort, weakness, dizziness, and/or giddiness. In addition, the patient can select a level of activity (e.g., light activity, moderate activity, rigorous activity, etc.) that he or she was performing when the symptom occurred. In some implementations, in response to the selection by the patient, the cardiac monitor can cause a portion of patient physiological information (e.g., in the form of a cardiac signal) to be captured for a length of time that is based on when the symptom was experienced. For example, the cardiac monitor can cause a portion of an ECG signal of the patient to be captured. In some implementations, the cardiac monitor can continuously record ECG data, and at the same time also identify and record one or more flags associated with portions of the ECG data relating to one or more events of interest (e.g., patient-reported symptoms, events detected by the patient monitor, among others.). As such, if a caregiver wishes to view ECG data for a period of time prior to or after the recorded ECG strip relating to an event of interest, such data is available for review from the continuously-recorded ECG data.

Pacing Processes

Figure 5:
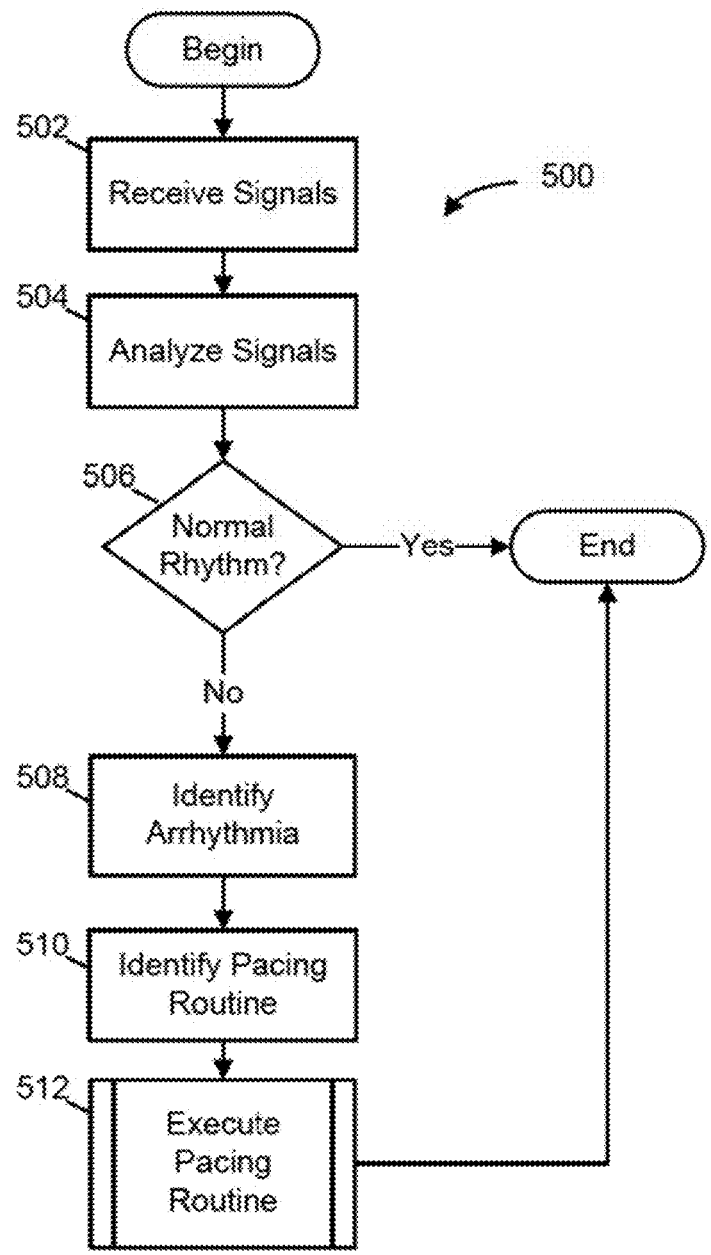
FIG. 5 is a flow diagram of one example of a process for pacing a subject.

As described above, various examples implement processes through which a medical device paces a subject using enhanced cardiac data. FIG. 5 illustrates one such pacing process 500 that utilizes enhanced cardiac data to pace a subject.

In act 502, a pacing device (e.g., the pacing device 100 of FIG. 1) receives acoustic and electrode signals generated from detectable characteristics of the subject's cardiac function via one or more electrodes (e.g., the electrode 120 of FIG. 1), one or more acoustic sensors (e.g., the acoustic sensor 122 of FIG. 1), or both. In act 504, the pacing device analyzes the received signals using an acoustic signal processing component (e.g., the acoustic signal processing component 124 of FIG. 1) and an electrode signal processing component (e.g., the electrode signal processing component 126 of FIG. 1) and a cardiac function analyzer (e.g., the cardiac function analyzer 112 of FIG. 1).

In act 506, the cardiac function analyzer determines whether the subject's cardiac rhythm is normal. If so, the process 500 ends. Otherwise, the cardiac function analyzer identifies the arrhythmia in act 508. In act 510, the cardiac function analyzer identifies a pacing routine associated with the identified arrhythmia by, for example, referring to a configurable parameter stored in data storage (e.g., the data storage 104 of FIG. 1).

In act 512, the cardiac function analyzer initiates execution of the identified pacing routine and the process 500 ends. The process 500 may execute repeatedly during operation of the pacing device to monitor and treat the subject as needed. The following sections describe processes that may be executed within the act 512.

Fixed Rate and Energy Pacing

Figure 7:
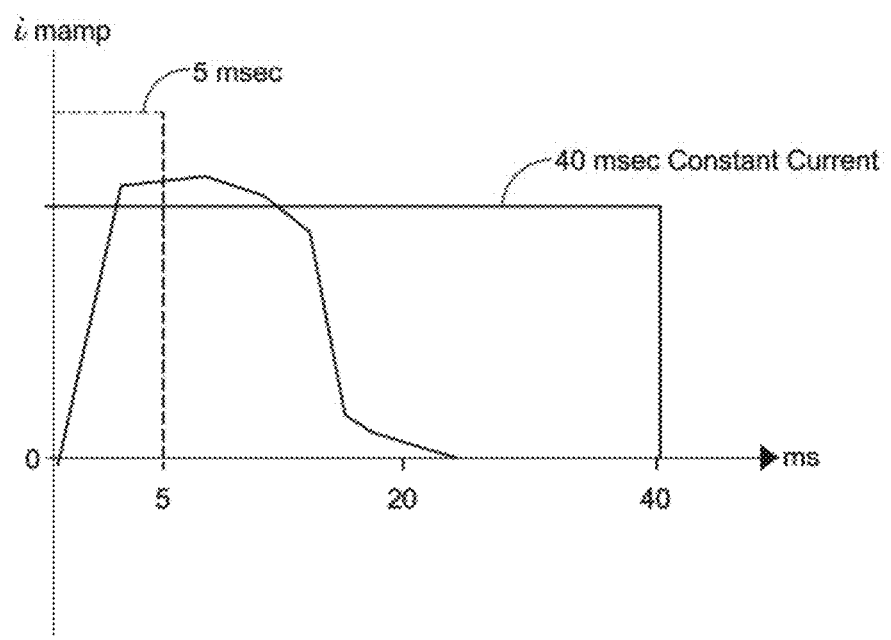
FIG. 7 is an illustration of a number of different pacing waveforms that may be provided by the medical monitoring and treatment device, including a 40 ms constant current pulse.

In accordance with one example of the act 512, a pacing device, such as the LifeVest® wearable cardioverter defibrillator, is configured to pace the heart of a subject at a fixed rate and fixed energy in response to various types of cardiac arrhythmias. Examples of these cardiac arrhythmias include bradyarrythmia, a lack of sensed cardiac activity (spontaneous or post shock asystole), and pulseless electrical activity. In some cases, these cardiac arrhythmias may occur before or after one or more defibrillation shocks. For example, the device may be configured to provide pulses at a fixed energy level, a fixed pulse width, and a fixed frequency in response to detection of any of the above-noted events via the ECG sensing electrodes 120 or the acoustic sensors 122. The energy level of the pacing pulses may be set to a fixed value by applying a desired current waveform for a determined duration of time by one or more of the plurality of therapy electrodes 214. The maximum current level of the current waveform may be set to a value between approximately 0 mAmps to 200 mAmps, the pulse width may be set to a fixed value between approximately 0.05 ms to 2 ms, and the frequency of the pulses may be set to a fixed value between approximately 30 pulses per minute (PPM) to approximately 200 PPM. In accordance with one example, a 40 ms square wave pulse is used. Example pacing current waveforms, including a 40 ms constant current pulse, a 5 ms constant current pulse, and a variable current pulse are shown in FIG. 7.

During pacing operation of the pacing device, the device may periodically pause for a period of time to evaluate the subject via the ECG sensing electrodes and the acoustic sensors to determine whether a normal sinus rhythm has returned. Where the device detects a normal sinus rhythm, the device may discontinue the application of pacing pulses and simply continue monitoring the subject's physiological signals, such as the subject's ECG, temperature, pulse oxygen level, respiration, etc. Where the device detects an arrhythmia that requires defibrillation, the device may begin a defibrillation treatment protocol potentially culminating in a defibrillating shock.

During an initial fitting of the pacing device, the level of current, the pulse width, and the frequency of the pulses may be set to an appropriate level based on the input of a medical professional (such as the subject's cardiologist) and the physiological condition of the subject (e.g., based on the subject's normal resting heart rate, the subject's thoracic impedance, etc.) In some examples, the level of current, the pulse width, and the frequency of the pulses may simply be set to an appropriate value based on typical impedance values for an adult or child, and typical resting heart rates for an adult or child.

It should be appreciated that because pacing at a fixed rate may interfere with the subject's own intrinsic heart rate, the device can be configured to perform such fixed rate and energy pacing only in the event of a life-threatening Bradyarrythmia, a lack of any detected cardiac activity following shock, or in response to pulseless electrical activity following a shock.

Demand (Adjustable Rate) Pacing

In accordance with one example of the act 512, a pacing device, such as the LifeVest® wearable cardioverter defibrillator, is configured to pace the heart of a subject at a variable rate and a fixed energy in response to various types of cardiac arrhythmias, including a bradyarrythmia (i.e., an excessively slow heart rate), tachycardia (i.e., an excessively fast heart rate), an erratic heart rate with no discernible regular sinus rhythm, a lack of sensed cardiac activity (asystole), and pulseless electrical activity. Some of these cardiac arrhythmias may occur following one or more defibrillation shocks.

As known to those skilled in the art, pacing at a fixed rate and energy may not be appropriate for the particular type of cardiac arrhythmia of the subject, and even where the rate and energy level is appropriate, pacing at a fixed rate can result in competition between the rate at which the pacing pulses are being applied and the intrinsic rhythm of the subject's heart. For example, pacing at a fixed rate may result in the application of a pacing pulse during the relative refractory period of the normal cardiac cycle (a type of R wave on a T wave effect) that could promote ventricular tachycardia or ventricular fibrillation. To overcome some of the disadvantages of fixed rate and energy pacing, the pacing device can be configured to perform demand pacing, wherein the rate of the pacing pulses may be varied dependent on the physiological state of the subject. For example, during demand pacing, the device can deliver a pacing pulse only when needed by the subject. In general, when executing in demand mode, the device searches for any intrinsic cardiac activity of the subject, and if a heartbeat is not detected within a designated interval, a pacing pulse is delivered and a timer is set to the designated interval. Where the designated interval expires without any detected intrinsic cardiac activity of the subject, another pacing pulse is delivered and the timer reset. In some examples, where an intrinsic heartbeat of the subject is detected within the designated interval, the device resets the timer and continues to search for intrinsic cardiac activity.

Figure 8:
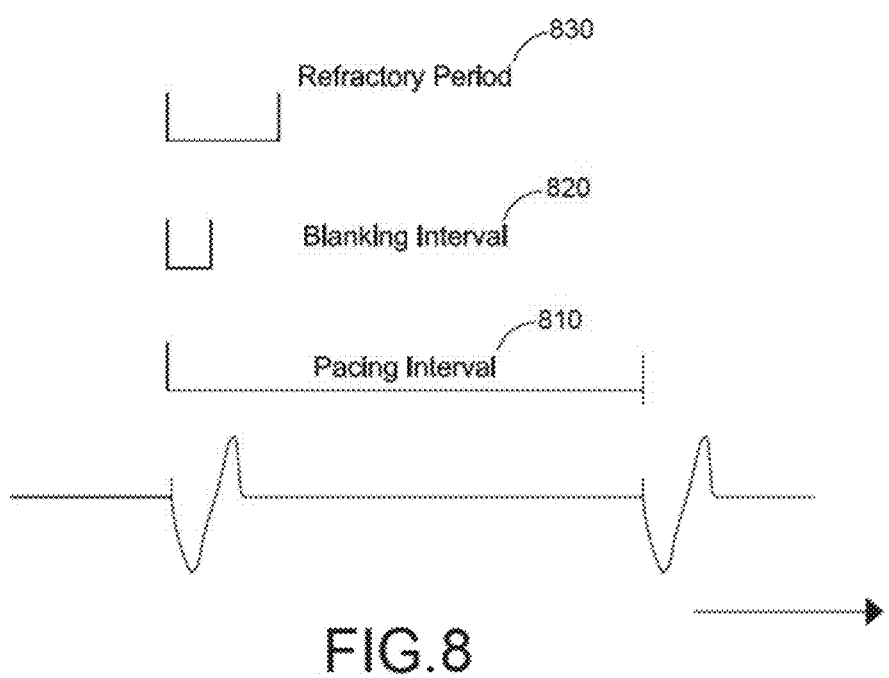
FIG. 8 is an illustration of various aspects of demand pacing which can be adjusted in connection with on demand pacing or capture management pacing.

FIG. 8 helps to illustrate some of the aspects of demand pacing and the manner in which demand pacing can be performed by the pacing device. As illustrated in FIG. 8, the device may have a variable pacing interval 810 corresponding to the rate at which pacing pulses are delivered to the subject in the absence of any detected intrinsic cardiac activity detected by the cardiac function analyzer 112. For example, the rate at which pulsing paces are to be delivered to the subject (referred to as the "base pacing rate" herein) may be set at 60 PPM and therefore, the corresponding base pacing interval 810 would be set to 1 second.

The pacing device may also have a hysteresis rate (not shown in FIG. 8) corresponding to the detected intrinsic heart rate of the subject below which the device performs pacing. According to some examples, the hysteresis rate is a configurable parameter that is expressed as a percentage of the subject's intrinsic heart rate. In the above example, the hysteresis rate may correspond to 50 beats per minute (BPM). In this example, if the intrinsic heart rate of the subject fell to 50 BPM or below (e.g., more than approximately 1.2 seconds between detected beats), the device would generate and apply a pacing impulse to the subject.

During application of a pacing pulse to the body of a subject and a short time thereafter, the pacing device may intentionally blank out a portion of the ECG signals being received by the ECG monitoring and detection circuitry (e.g., the electrode 120 and the electrode signal processing component 126 described above) to prevent this circuitry (e.g., amplifiers, A/D converters, etc.) from being overwhelmed (e.g., saturated) by the pacing pulse. This may be performed in hardware, software, or a combination of both. This period of time, referred to herein as "the blanking interval" 820 may vary (e.g., between approximately 30 ms to 200 ms), but is typically between approximately 40 ms to 80 ms in duration. In some examples, the cardiac function analyzer 112 overcomes the inability to detect cardiac function via ECG sensing electrodes during the blanking interval by referencing the processed acoustic data to detect cardiac function during the blanking interval.

In addition to the blanking interval 820, the pacing device can have a variable refractory period 830 that may vary dependent upon the base pacing rate. The refractory period 830 corresponds to a period of time in which signals sensed by the ECG sensing electrodes 120 or the acoustic sensor 122 are ignored, and may include the blanking interval. The refractory period 830 allows any generated QRS complexes or T waves induced in the subject by virtue of the pacing pulse to be ignored, and not interpreted as intrinsic cardiac activity of the subject. For example, where the base pacing rate is set to below 80 PPM, the refractory period might correspond to 240 ms, and where the base pacing rate is set above 90 PPM, the refractory period might correspond to 240 ms. For typical applications, the refractory period is generally between about 150 ms and 400 ms.

In one example, the sensitivity of the ECG monitoring and detection that is performed by the pacing device may also be varied to adjust the degree by which the ECG monitoring and detection circuitry can detect the subject's intrinsic cardiac activity. For example, where the amplitude of certain discernible portions (e.g., an R-wave) of a subject's intrinsic ECG signal is below that typically encountered, the voltage threshold over which this discernible portion can be detected as belonging to an ECG signal (and not attributed to noise or other factors) may be lowered, for example from 2.5 mV to 1.5 mV, to better detect the subject's intrinsic cardiac activity. For instance, during an initial fitting of the pacing device, the sensitivity threshold of the device may be reduced to a minimal value (e.g., 0.4 mV) and the subject's intrinsic ECG signals may be monitored. The sensitivity threshold may then be incrementally increased (thereby decreasing the sensitivity of the device) and the subject's intrinsic ECG signals monitored until these ECG signals are no longer sensed. The sensitivity threshold may then be incrementally decreased (thereby increasing the sensitivity of the device) until the subject's intrinsic ECG signals are again sensed, and the sensitivity threshold of the device may be set to approximately half this value.

In one example, the sensitivity of the acoustic monitoring and detection that is performed by the pacing device may also be varied to adjust the degree by which the acoustic monitoring and detection circuitry (e.g., the acoustic sensor 122 and the acoustic signal processing component 124) can detect the subject's intrinsic cardiac activity. For example, where the amplitude of certain discernible portions of a subject's intrinsic heart sound signal is below that typically encountered, the noise threshold over which this discernible portion can be detected as belonging to a heart sound signal (and not attributed to noise or other factors) may be lowered to better detect the subject's intrinsic cardiac activity. For instance, during an initial fitting of the pacing device, the sensitivity threshold of the device may be reduced to a minimal value and the subject's intrinsic heart sound signals may be monitored. The sensitivity threshold may then be incrementally increased (thereby decreasing the sensitivity of the device) and the subject's intrinsic heart sound signals monitored until these heart sound signals are no longer sensed. The sensitivity threshold may then be incrementally decreased (thereby increasing the sensitivity of the device) until the subject's intrinsic heart sound signals are again sensed, and the sensitivity threshold of the device may be set to approximately half this value.

As with fixed energy and rate pacing, the device may be configured to provide pulses at a fixed energy level and a fixed pulse width in response to detection of any of the above-noted events by the cardiac function analyzer 112. The maximum current level of the current waveform may be set to a value between approximately 10 mAmps to 200 mAmps, the pulse width may be set to a fixed value between approximately 20 ms to 40 ms, and the base rate of the pulses may be set to a fixed value between approximately 30 pulses per minute (PPM) to approximately 200 PPM, although the actual rate of the pacing pulses can vary based upon the intrinsic cardiac activity of the subject. In accordance with one example, a 40 ms constant current pulse is used, and the current level is set to a fixed value based upon the input of a medical professional, such as the subject's cardiologist and the physiological condition of the subject. The base pacing rate and the hysteresis rate may also be set based upon the input of the subject's cardiologist (or other medical professional) and the physiological condition of the subject, and the blanking interval and refractory period set to an appropriate time interval based upon the base pacing rate and/or the hysteresis rate.

Although the base pacing rate may be set to a particular value based on the physiological condition of the subject and input from a medical profession, the pacing device can include a number of different pacing routines to respond to different cardiac arrhythmias, such as bradycardia, tachycardia, an erratic heart rate with no discernible regular sinus rhythm, asystole, or pulseless electrical activity. These pacing routines may be implemented using a variety of hardware and software components and examples are not limited to a particular configuration of hardware or software. For instance, the pacing routines may be implemented using an application-specific integrated circuit (ASIC) tailored to perform the functions described herein.

Demand Pacing—Bradycardia

As discussed above, where Bardycardia is detected and the intrinsic cardiac rate of the subject is below that of the hysteresis rate, the pacing device will pace the subject at the pre-set base pacing rate. During this time, the device will continue to monitor the subject's intrinsic heart rate and will withhold pacing pulses in the event that an intrinsic heartbeat is detected within designated interval corresponding to the hysteresis rate. This type of on demand pacing is frequently termed "maintenance pacing."

Demand Pacing—Tachycardia

For responding to tachycardia, the pacing device may additionally include another pacing rate, termed an "antitachyarrhythmic pacing rate" herein, above which the device will identify that the subject is suffering from tachycardia, and will pace the subject in a manner to bring the subject's intrinsic heart back toward the base racing rate. For example, the device may employ a technique known as overdrive pacing wherein a series of pacing pulses (e.g., between about 5 and 10 pacing pulses) are delivered to the subject at a frequency above the intrinsic rate of the subject in an effort to gain control of the subject's heart rate. Once it is determined that the device is in control of the subject's heart rate, the rate (i.e., the frequency) of the pulses may be decremented, for example by about 10 ms, and another series of pacing pulses delivered. This delivery of pulses and the decrease in frequency may continue until the detected intrinsic cardiac rate of the subject is below the antitachyarrhythmic pacing rate. This type of pacing is frequently termed "overdrive pacing" or "fast pacing."

Demand Pacing—Erratic Heart Rate

For responding to an erratic heart rate, the pacing device may perform a type of pacing that is similar to a combination of maintenance pacing and overdrive pacing discussed above. For example, where the pacing device detects an erratic heart rate with no discernible sinus rhythm, the device may deliver a series of pacing pulses (e.g., between about 5 and 10 pacing pulses) to the subject at a particular frequency. This frequency may be one that is above a lower frequency of a series of detected intrinsic beats of the subject's heart and below an upper frequency of the detected intrinsic beats of the subject's heart. After delivering the series of pulses, the device may monitor the subject's heart to determine if it has synchronized to the rate of the series of delivered pulses. Where the intrinsic rate of the subject's heart is still erratic, the device may increase the frequency of the series of pulses and deliver another series. This may continue until it is established that the subject's heart assumes a more regular state. Upon determining that the subject's heart is in a more regular state, the device may perform maintenance pacing if it is determined that the subject's intrinsic heart rate is too low as discussed in the "Demand Pacing—Bradycardia" section above, or perform pacing at a decremented rate in the manner discussed in "Demand Pacing—Tachycardia" section above, if such is warranted.

Demand Pacing—Asystole or Pulseless Electrical Activity

For responding to asystole or a detected condition of pulseless electrical activity, the pacing device may perform maintenance pacing similar to that described in the "Demand Pacing—Bradycardia" section above. This type of pacing would be performed after a series of one or more defibrillating shocks that attempt to restore a normal sinus rhythm to the heart of the subject.

In each of the types of pacing described above, the pacing device may be configured to perform a particular type of pacing only after a programmable delay after such cardiac arrhythmias are detected, or after a programmable period of time after one or more defibrillating shocks are delivered.

Capture Management

In one example of the act 512, a pacing device, such as the LifeVest® wearable cardioverter defibrillator, is configured to pace the heart of a subject using capture management with an adjustable energy level and an adjustable rate in response to various types of cardiac arrhythmias. The various types of cardiac arrhythmias can include a bradycardia, tachycardia, an erratic heart rate with no discernible regular sinus rhythm, a lack of sensed cardiac activity (asystole) following or independent of one or more defibrillation shocks, a life-threatening Bradyarrythmia following one or more defibrillation shocks, or pulseless electrical activity following one or more defibrillation shocks.

As known to those skilled in the art, capture management refers to a type of pacing in which the energy level of pacing pulses and the rate of delivery of those pacing pulses may be varied based upon the detected intrinsic activity level of the subject's heart and the detected response of the subject's heart to those pacing pulses. In cardiac pacing, the term "capture" is used to refer to the response of a subject's heart to a pulse of energy which results in ventricular depolarization. In cardiac pacing, it is desirable to limit the amount of energy in each pulse to a minimal amount required for capture; thereby minimizing the amount of discomfort associated with external pacing.

In general, the manner in which the pacing device performs capture management pacing is similar to that of demand pacing described above, in that it may adjust the rate at which pacing pulses are delivered based upon the detected intrinsic rate of cardiac activity of the subject. The sensitivity of the device to the subject's ECG and heart sounds may be adjusted in a similar manner to that described above with respect to demand pacing. Further, capture management pacing may be used to treat the same types of cardiac arrhythmias as the demand pacing described above, such as bradycardia, tachycardia, an erratic heart rate with no discernible sinus rhythm, asystole, or pulseless electrical activity.

However, in contrast to a device that performs demand pacing, a device that is configured to perform capture management pacing will typically have a refractory period 830 (see FIG. 8) that is significantly shorter than a device configured to perform demand pacing. Indeed, when using capture management pacing, there may be no refractory period 830 at all, but only a blanking interval 820. In some examples, where there is a refractory period 830, the refractory period 830 may be similar in duration to the blanking interval 820. As would be appreciated by those skilled in the art, this is because during capture management pacing, the response of the subject's heart is monitored by the cardiac function analyzer 112 to detect whether the delivered pulse of energy resulted in capture. For this reason, while the ECG monitoring and detection circuitry may be switched off or effectively disabled during the delivery of energy pulses, the acoustic monitoring and detection circuitry can be relied upon to detect whether the delivered pulse resulted in capture.

During capture management pacing, the pacing device can initially deliver a pulse of energy at a predetermined, low energy level and monitor the subject's response to determine if capture resulted. Where it is determined that the delivered pulse did not result in capture, the energy level of the next pulse may be increased. For example, where the device is a pacing device that is external to the subject, the initial setting may be configured to provide a 40 ms rectilinear and constant current pulse of energy at a current of 40 mAmps, and increase the amount of current in increments of 2 mAmps until capture results. The next pacing pulse may be delivered at increased current relative to the first pacing pulse and at a desired rate relative to the first pacing pulse in the absence of any detected intrinsic cardiac activity of the subject. Where the next pacing pulse does not result in capture, the energy may be increased until capture is detected. The pacing device may then continue pacing at this energy level and at a desired rate in the absence of any detected intrinsic cardiac activity of the subject. During this period of time, the device monitors the subject's cardiac response to the pacing pulses, and may increment the energy level further, should it be determined over one or more subsequent pulses that capture did not result.

In one example, the pacing device may apply a series of pulses at an initial energy level and rate, and monitor the subject's response to determine if capture resulted. Where capture did not result, or where capture resulted in response to some of the pulses, but not all, the device may increase the energy of a next series of pulses until capture results for each pulse.

In some examples, the device may be configured to identify a minimum amount of energy that results in capture during capture management pacing. Where it is determined that the delivered pulse did result in capture, the energy level of the next pulse may be decreased. For example, where the device is a pacing device that is external to the subject, the initial setting may be configured to provide a 40 ms constant current pulse of energy at a current of 70 mAmps. Where it is determined that the delivered pulse resulted in capture, subsequent pacing pulse may be delivered at decreased in increments of 5 mAmps and at a desired rate relative to the first pacing pulse in the absence of any detected intrinsic cardiac activity of the subject until capture is no longer achieved. Where the next pacing pulse does not result in capture, the energy setting may be increased to the last current known to produce a pulse resulting in capture, and then delivering a pulse at the higher energy setting, thus delivering the minimal amount of energy required for capture. The pacing device may then continue pacing at this energy level and at a desired rate in the absence of any detected intrinsic cardiac activity of the subject. During this period of time, a similar routine may be re-performed at predetermined intervals to ensure that the minimum amount of energy is being delivered for capture. In addition, during this period of time, the device monitors the subject's cardiac response to the pacing pulses, and may increase the energy level should it be determined over one or more subsequent pulses that capture did not result.

Figure 6:
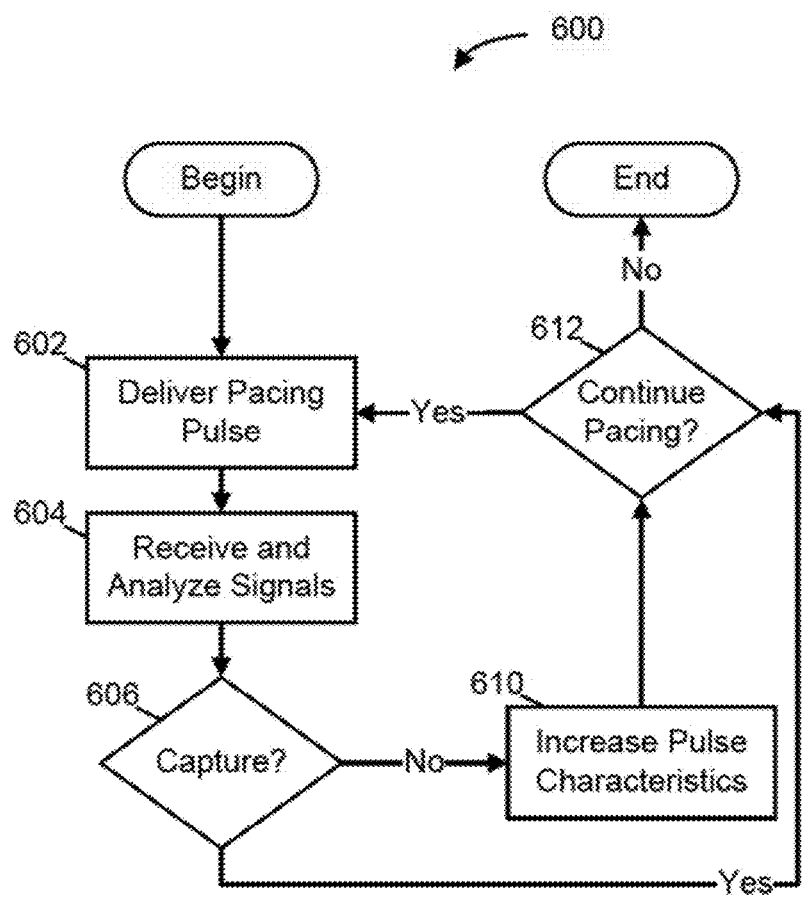
FIG. 6 is a flow diagram of one example of another process for pacing a subject.

FIG. 6 illustrates one example of a capture management process 600 that is executed with the act 512 and that utilizes enhanced cardiac data (electrode and acoustic data) to pace a subject.

In act 602, the pacing device delivers one or more pacing pulses to the subject. In act 604, the pacing device receives (via the one or more electrodes and one or more acoustic sensors) and analyzes (via the acoustic signal processing component, the electrode signal processing component, and the cardiac function analyzer) acoustic and electrode signals generated from detectable characteristics of the subject's cardiac function.

In act 606, the pacing device determines whether delivery of the one or more pacing pulses resulted in capture. The cardiac function analyzer may make this determination by analyzing processed electrode data, processed acoustic data, or by analyzing some combination of processed electrode data and processed acoustic data. For instance, if processed electrode data is not available, the cardiac function analyzer may determine the characteristics of the heat beat by identifying the presence and timing of known heart sounds, such as S1, S2 and the like.

FIGS. 9-12 are a graphical representation of ECG and acoustic signals acquired during animal testing. The testing was conducted with a wearable defibrillator, such as the model 4000 LifeVest® brand wearable defibrillator. During the testing, the animal was anesthetized and given a beta-blocker to establish a stable heart rate of 50 BPM. The wearable defibrillator was fitted to the animal and was configured to pace the animal at a rate faster than 50 BPM. Pacing sessions 60 seconds in duration were administered. The energy of the pacing pulses used varied between pacing sessions. In some pacing sessions, conductive gel was applied to the animal. In other pacing sessions, conductive gel was not applied to the animal.

Figure 9:
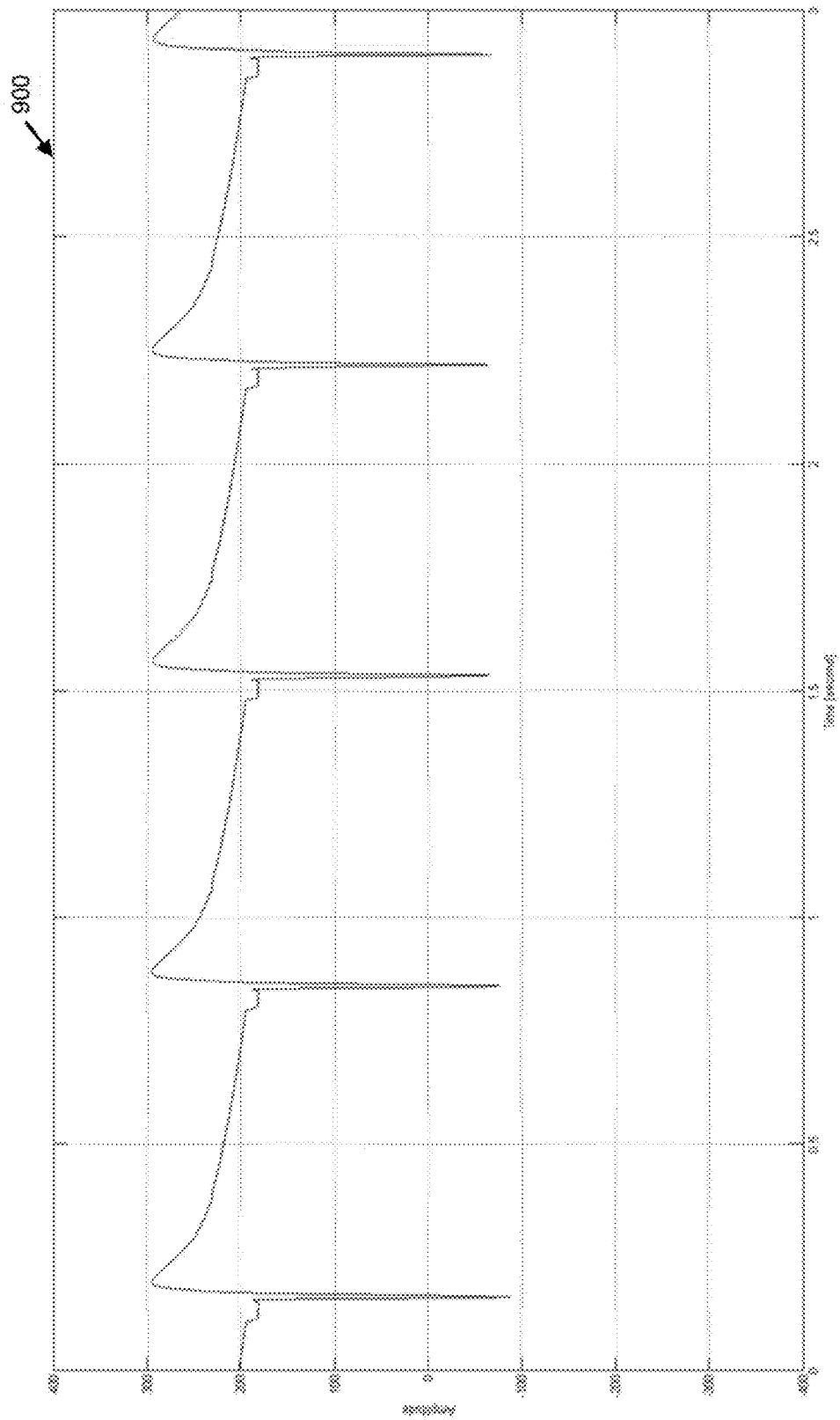
FIG. 9 is an illustration of an electrical signal acquired during execution of a pacing process.
Figure 10:
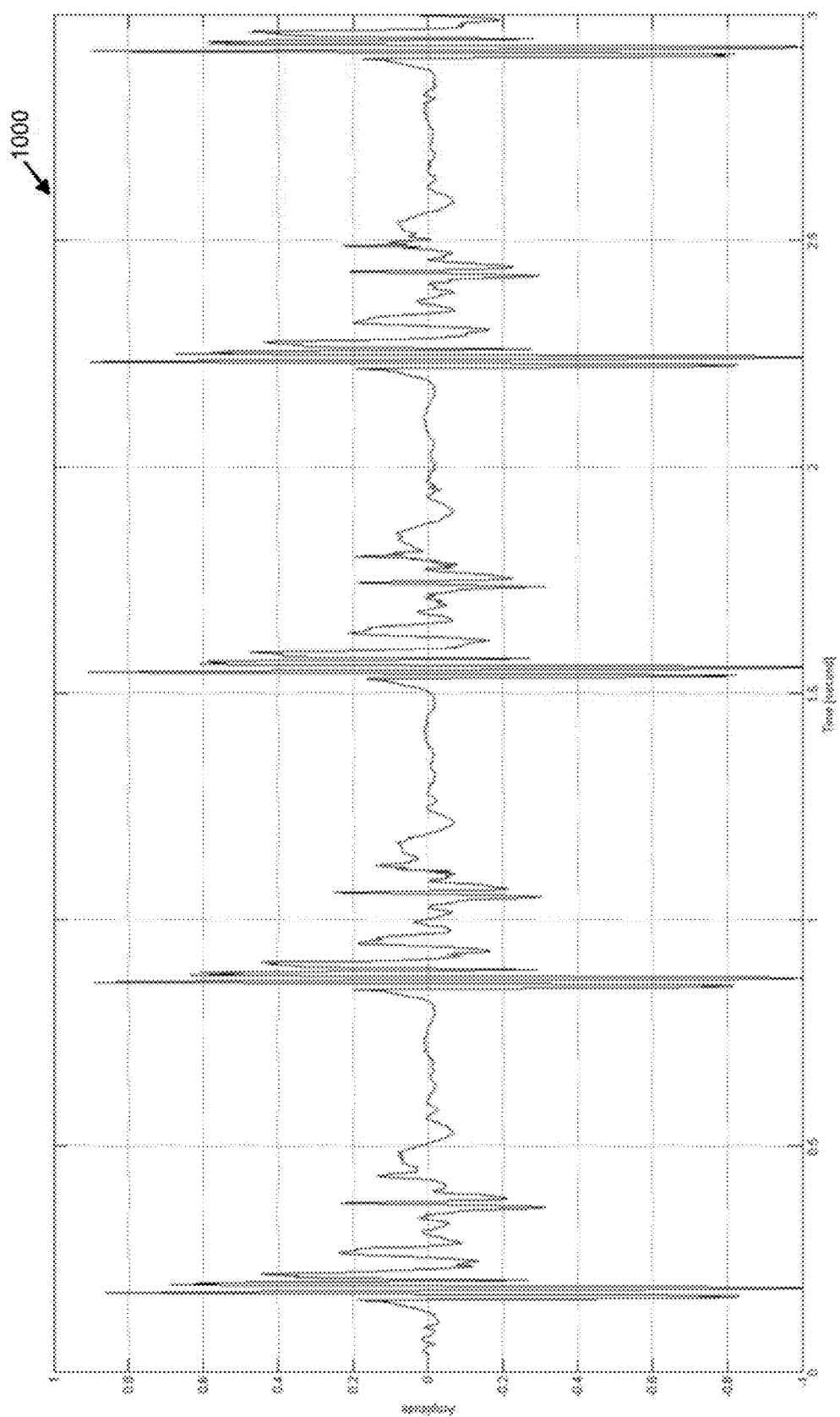
FIG. 10 is an illustration of an acoustic signal acquired during execution of a pacing process.
Figure 11:
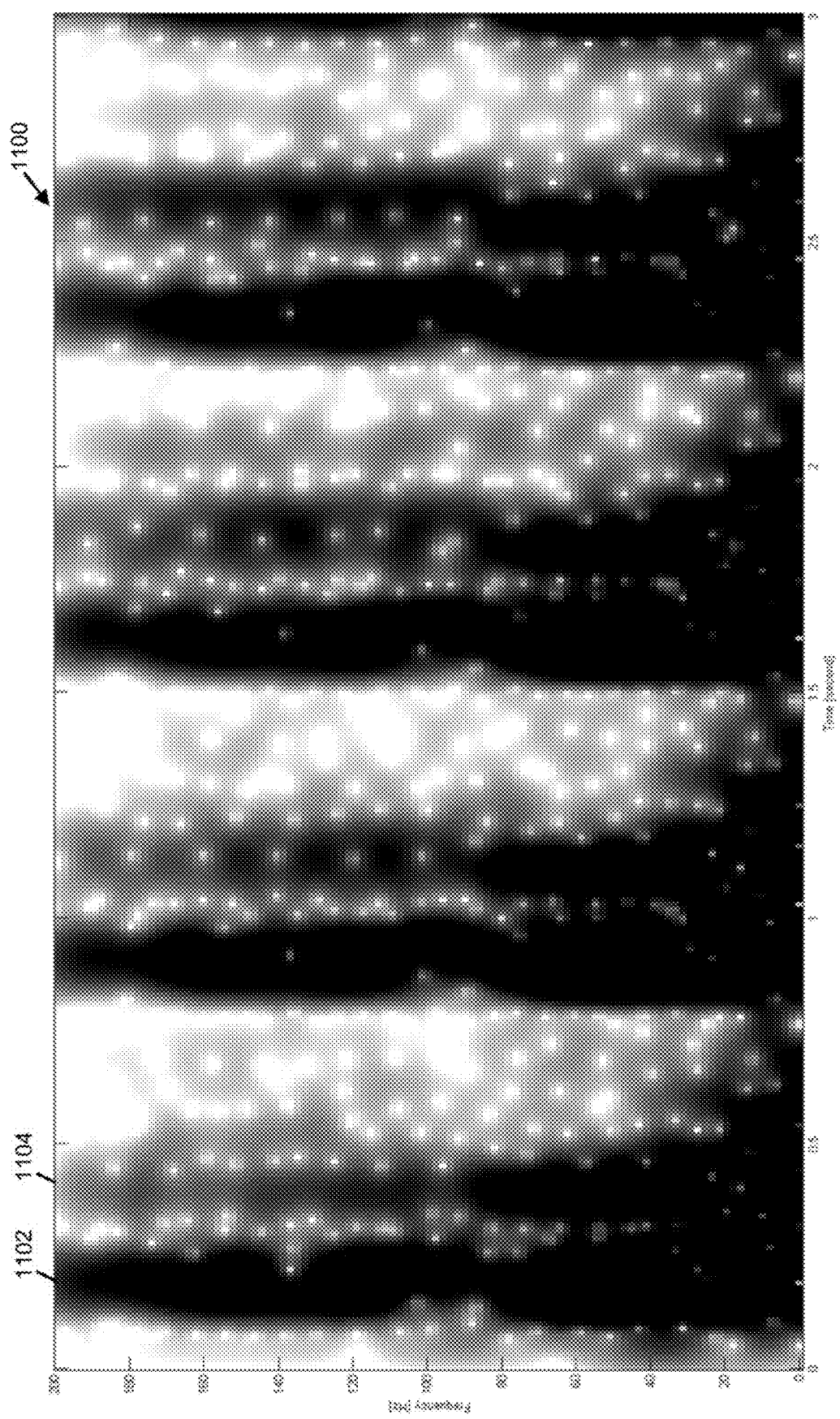
FIG. 11 is another illustration of an acoustic signal acquired during execution of a pacing process.
Figure 12:
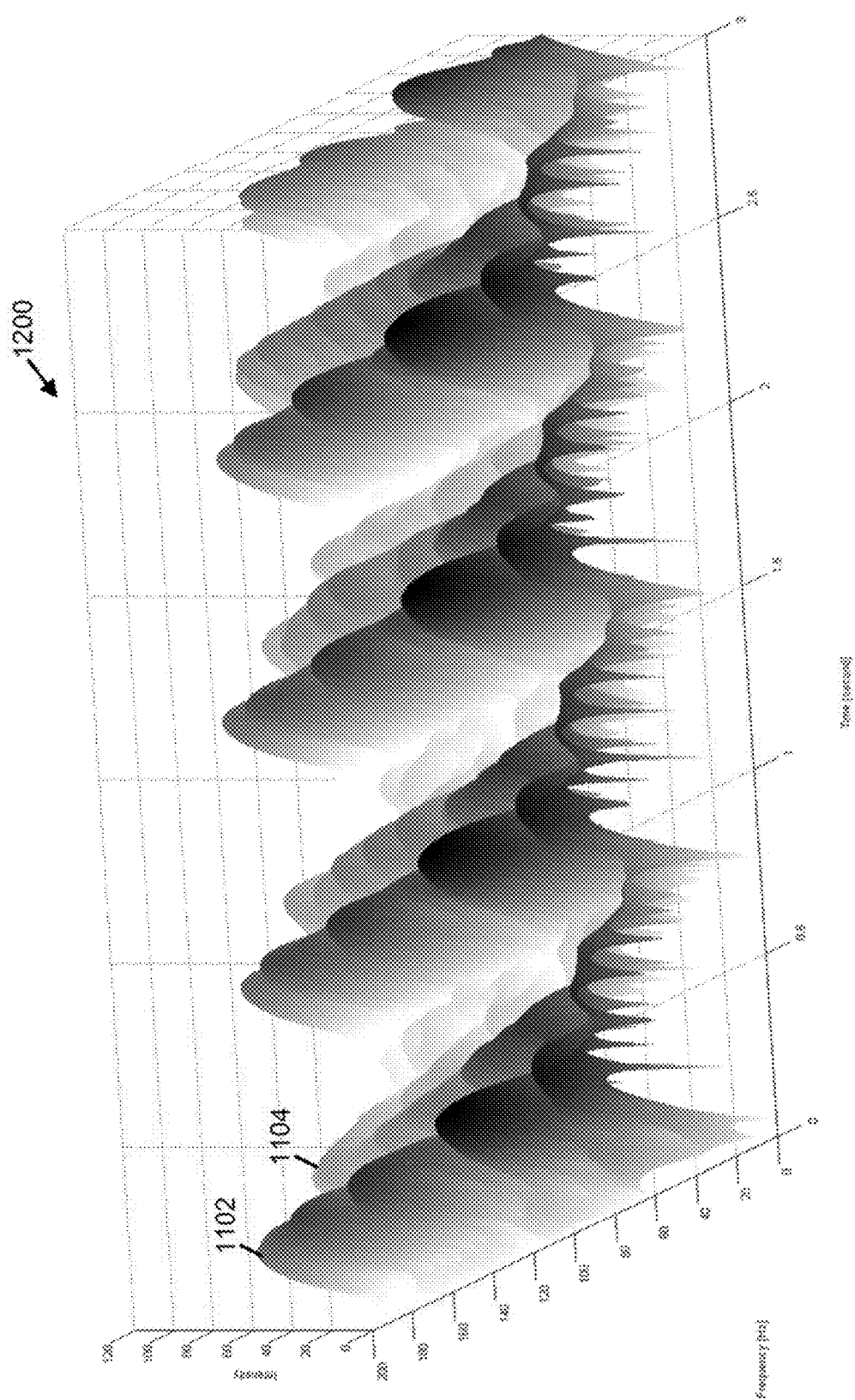
FIG. 12 is an another illustration of acoustic signal acquired during execution of a pacing process.

Plots 900, 1000, 1100, and 1200 illustrate signals acquired over a common time period during the animal testing described above. As shown in FIG. 9, plot 900 illustrates an acquired electrical signal. The x-axis of plot 900 indicates time in seconds. The y-axis of the plot 900 indicates amplitude (e.g., in millivolts). As shown in FIG. 10, plot 1000 illustrates an acquired acoustic signal. The x-axis of the plot 1000 indicates time in seconds. The y-axis of the plot 1000 indicates amplitude. As shown in FIG. 11, plot 1100 also illustrates the acquired acoustic signal. The x-axis of the plot 1100 indicates time in seconds. The y-axis of the plot 1100 indicates frequency in Hertz. The greyscale of the images in the plot 1100 indicate amplitude at the indicated time and frequency. As shown in FIG. 12, plot 1200 also illustrates the acquired acoustic signal. The x-axis of the plot 1100 indicates time in seconds. The y-axis indicates amplitude. The z-axis of the plot 1100 indicates frequency in Hertz. Within the plots 1100 and 1200, the peaks 1102 and 1104 respectively illustrate the sounds generated by the contraction of the heart (e.g., due to a corresponding pacing pulse) and the closure of semilunar valves. In some examples, the cardiac function analyzer is configured to detect capture by identifying the presence or the absence of the peak 1104. In at least one example, the cardiac function analyzer identifies the presence or absence of the peak 1104 by executing a capture detection process 1300 as illustrated in FIG. 13.

Figure 13:
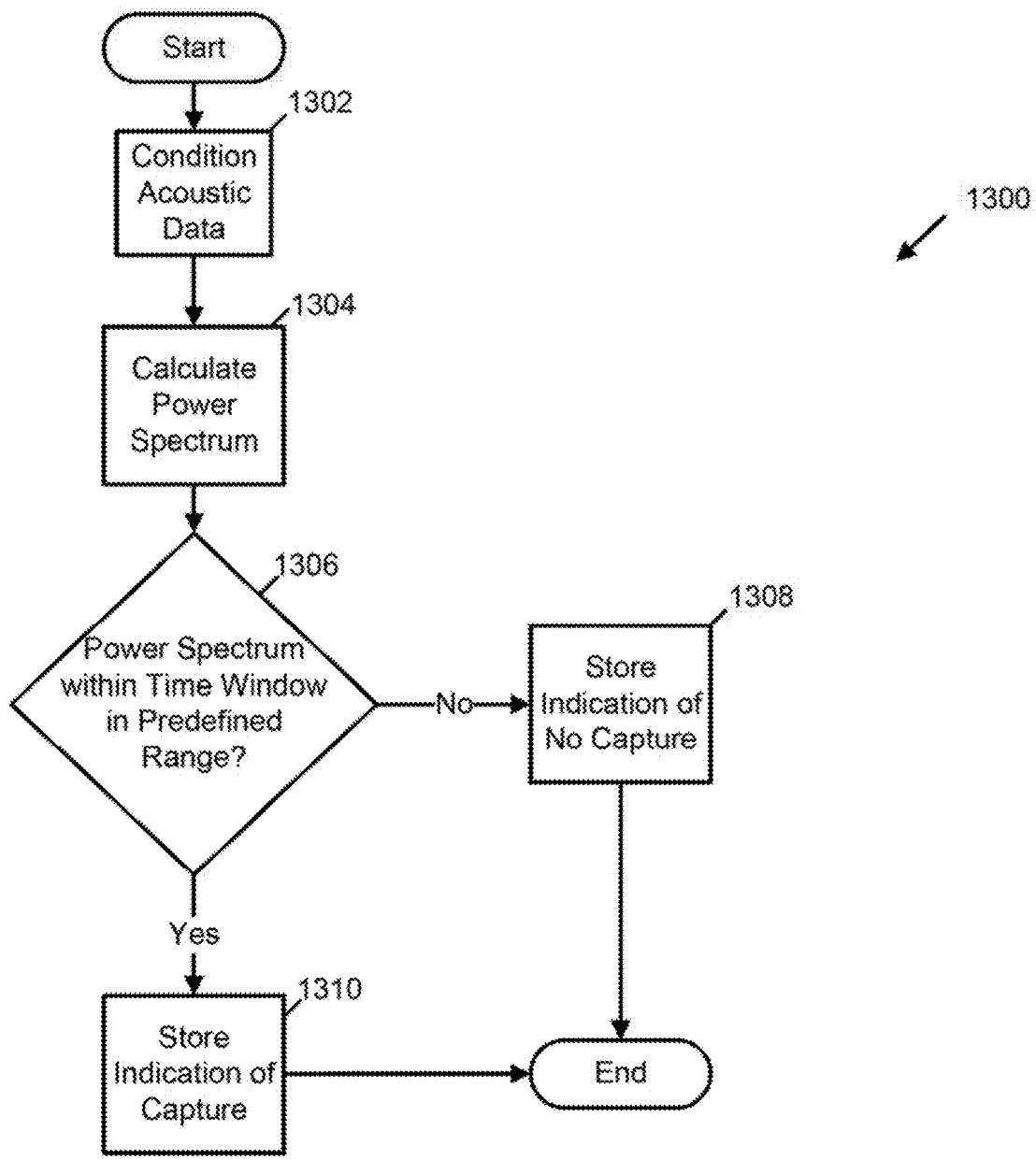
FIG. 13 is a flow diagram of a capture detection process.

As shown in FIG. 13, the capture detection process 1300 starts in act 1302 where the cardiac function analyzer performs any necessary conditioning of the processed acoustic data to ready the data for power spectrum analysis in act 1304. This conditioning may include, for example, processing the data with a band-stop filter to attenuate irrelevant frequencies (e.g., frequencies falling outside of a range of frequencies from 10 Hz to 250 Hz). In the act 1304, the cardiac function analyzer calculates a power spectrum (e.g., via a discrete Fourier transform) for relevant frequencies (e.g., frequencies falling inside a range of frequencies from 10 Hz to 250 Hz) acquired within a predefined time window following delivery of a pacing pulse. In act 1306, the cardiac function analyzer determines whether the power of each frequency bin in the power spectrum transgresses a corresponding, respective predefined threshold value or falls within a corresponding, respective predefined range of values. If the power of each frequency bin transgresses its corresponding, respective predefined threshold value or falls within its corresponding, respective predefined range of values, the cardiac function analyzer executes act 1310. If the power of any of the frequency bins does not fall within its corresponding, respective predefined range of values, the cardiac function analyzer executes act 1308.

In the act 1308, the cardiac function analyzer stores an indication of no capture in a data store of the pacing device and terminates the capture detection process 1300. In the act 1310, the cardiac function analyzer stores an indication of capture in a data store of the pacing device and terminates the capture detection process 1300.

Processes in accord with the capture detection process 1300 enable a pacing device to determine whether capture has occurred using an acoustic signal channel, thereby avoiding any electrical interference that may be caused by the delivery of a pacing pulse. Such processes may be executed in conjunction with each pacing pulse delivered by the pacing device. It is appreciated that capture detection processes such as the capture detection process 1300 may be executed by medical devices that do not have an integral treatment component. Such devices may include cardiac monitors having sensing electrodes, a medical device controller and/or other components that support monitoring a patient's cardiac cycle. Examples of such cardiac monitors include holter monitors, mobile cardiac telemetry (MCT) monitors, and/or continuous event monitoring (CEM) monitors. These cardiac monitors may, in some instances, interoperate with pacing devices such as external or internal pacing devices to record and/or report data descriptive of the effectiveness of the pacing devices including information regarding pacing capture.

Within the capture detection process 1300, the combination of acts 1304 and 1306 perform a power spectrum analysis of the acoustic data to determine whether capture has occurred. In other examples, other signal processing techniques may alternatively or additionally be used to detect capture. These other signal processing techniques may include time and frequency based derivative analysis, integration analysis, peak amplitudes analysis, and the like. In some examples, the values relevant to these other signal processing techniques are calculated in the act 1304 and are used to identify a threshold level of similarity between the acoustic data and benchmark acoustic data known to indicate capture in the act 1306.

Returning to FIG. 6, if delivery of the one or more pacing pulses did not result in capture, the cardiac function analyzer increases the pulse characteristics in act 610, thereby increasing the likelihood that the next one or more pacing pulses delivered will result in capture. In some examples of the act 610, the cardiac function analyzer does not infer capture has occurred until the subject's heart rate transgresses the subject's hysteresis rate for a predetermined period (e.g., 6 seconds or 5 heartbeats).

In act 612, the cardiac function analyzer determines whether further pacing is needed. If not, the capture management process 600 ends. Otherwise, the cardiac function analyzer returns to the act 602 and delivers the one or more pacing pulses to the subject. The process 600 may execute repeatedly during operation of the pacing device to monitor and treat the subject as needed.

It should be appreciated that in the various examples described above, an external pacing device has been described which may not only provide life saving defibrillation or cardioversion therapy, but may also provide a wide variety of different pacing regimens. Because the pacing device can monitor a subject's intrinsic cardiac activity, the subject's thoracic impedance, and other physiological characteristics of the subject, the device may be configured to recommend various settings to a medical professional for review and approval. The various settings that may be recommended may include a recommended base pacing rate, a recommended hysteresis rate, a recommended antitachyarrhythmic pacing rate, a recommended energy level (or initial energy level if capture management is used), a recommended blanking interval, and/or refractory period, and a recommended sensitivity threshold. In the case of a pacing device such as the LifeVest® cardioverter defibrillator, this initial recommendation may be performed when the subject is being fitted for and trained on the use of the device.

Although the ability to recommend such settings to a medical professional for their review and approval is particularly well suited to a pacing device, such as the LifeVest® cardioverter defibrillator, such functionality could also be implemented in an Automated External Defibrillator (AED) or an Advanced Life Support (ALS) type of defibrillator, such as the M Series defibrillator, R Series ALS defibrillator, R Series Plus defibrillator, or E Series defibrillator manufactured by the ZOLL Medical Corporation of Chelmsford Mass. It should be appreciated that monitoring the subject's intrinsic cardiac activity and other physiological characteristics and making recommendations to a trained medical professional for their review and approval (or possible modification) could reduce the amount of time that is spent manually configuring such devices prior to use on the subject.

Having thus described several aspects of at least one example of this disclosure, it is to be appreciated various alterations, modifications, and improvements will readily occur to those skilled in the art. Such alterations, modifications, and improvements are intended to be part of this disclosure, and are intended to be within the scope of the disclosure. Accordingly, the foregoing description and drawings are by way of example only.

The invention claimed is:

1. A wearable medical device comprising:
therapy electrodes comprising at least one front therapy electrode configured for placement on a front of a body of a subject and at least one back therapy electrode configured for placement on a back of the body of the subject; and
at least one processor coupled with the therapy electrodes and configured to:
during a defibrillation mode, cause the at least one front therapy electrode to be anodic and the at least one back therapy electrode to be cathodic; and
during a pacing mode, for at least one of a plurality of therapeutic phases of a pacing pulse, cause the at least one front therapy electrode to be cathodic and the at least one back therapy electrode to be anodic.

2. The wearable medical device of claim 1, further comprising a switching circuit coupled with the at least one processor, the switching circuit comprising a plurality of switches for controlling a polarity of the at least one back therapy electrode and the at least one front therapy electrode.

3. The wearable medical device of claim 2, wherein the switching circuit comprises an H-bridge circuit.

4. The wearable medical device of claim 2, wherein the switching circuit comprises one or more switch driver circuits to control a switch state of one or more of the plurality of switches.

5. The wearable medical device of claim 4, wherein the at least one processor is further configured to provide a phase profile to the one or more switch driver circuits to control the switch state of the one or more of the plurality of switches.

6. The wearable medical device of claim 1, wherein the at least one processor is further configured to cause delivery of the pacing pulse via the at least one front therapy electrode and the at least one back therapy electrode, and wherein a duration of the pacing pulse is between about 2-120 ms.

7. The wearable medical device of claim 6, wherein the at least one processor is further configured to cause delivery of a defibrillation pulse during the defibrillation mode via the at least one front therapy electrode and the at least one back therapy electrode, and wherein a duration of the defibrillation pulse is about 10 ms.

8. The wearable medical device of claim 1, further comprising at least one acoustic sensor, wherein the at least one processor is further configured to analyze processed acoustic data received via the at least one acoustic sensor to determine whether the pacing pulse resulted in capture.

9. The wearable medical device of claim 8, wherein the at least one processor is configured to analyze the processed acoustic data by recording acoustic signals during a blanking interval.

10. The wearable medical device of claim 1, further comprising one or more ECG sensing electrodes configured for placement at various locations on the body of the subject.

11. The wearable medical device of claim 1, further comprising a garment configured to worn about the torso of the subject, wherein the at least one front therapy electrode is configured for placement on the front of the body of the subject by being coupled to a front portion of the garment, and the at least one back therapy electrode is configured for placement on the back of the body of the subject by being coupled to a back portion of the garment.

12. A wearable medical device comprising:
    therapy electrodes comprising at least one front therapy electrode configured for placement on a front of a body of a subject and at least one back therapy electrode configured for placement on a back of the body of the subject; and
    at least one processor coupled with the therapy electrodes and configured to:
        during a defibrillation mode, cause the therapy electrodes to deliver a defibrillation pulse to the body of the subject; and
        during a pacing mode, for at least one of a plurality of therapeutic phases of a pacing pulse, cause a change in a polarity of the at least one front therapy electrode from anodic to cathodic, and cause a change in a polarity of the at least one back therapy electrode from cathodic to anodic.

13. The wearable medical device of claim 12, wherein the defibrillation pulse is a biphasic defibrillation pulse.

14. The wearable medical device of claim 12, further comprising a switching circuit in communication with the at least one processor, the switching circuit comprising a plurality of switches for controlling a polarity of the at least one back therapy electrode and the at least one front therapy electrode.

15. The wearable medical device of claim 14, wherein the switching circuit comprises an H-bridge circuit.

16. The wearable medical device of claim 14, wherein the switching circuit comprises one or more switch driver circuits to control a switch state of one or more of the plurality of switches.

17. The wearable medical device of claim 16, wherein the at least one processor is further configured to provide a phase profile to the one or more switch driver circuits to control the switch state of the one or more of the plurality of switches.

18. The wearable medical device of claim 12, wherein the at least one processor is further configured to cause delivery of the pacing pulse via the at least one front therapy electrode and the at least one back therapy electrode, and wherein a duration of the pacing pulse is between about 2-120 ms.

19. The wearable medical device of claim 18, wherein a duration of the defibrillation pulse is about 10 ms.

20. The wearable medical device of claim 12, further comprising at least one acoustic sensor, wherein the at least one processor is further configured to analyze processed acoustic data received via the at least one acoustic sensor to determine whether the pacing pulse resulted in capture.

21. The wearable medical device of claim 12, further comprising one or more ECG sensing electrodes configured for placement at various locations on the body of the subject.

22. The wearable medical device of claim 12, further comprising a garment configured to worn about the torso of the subject, wherein the at least one front therapy electrode is configured for placement on the front of the body of the subject by being coupled to a front portion of the garment, and the at least one back therapy electrode is configured for placement on the back of the body of the subject by being coupled to a back portion of the garment.

* * * * *